(12) United States Patent
Baba et al.

(10) Patent No.: US 6,381,299 B1
(45) Date of Patent: Apr. 30, 2002

(54) X-RAY EXAMINATION APPARATUS AND IMAGING METHOD OF X-RAY IMAGE

(75) Inventors: Rika Baba, Kokubunji; Ken Ueda, Ome; Hiroyuki Kawai, Tokyo; Hironori Ueki, Kokubunji; Koichi Koike, Kashiwa; Akira Kuba, Nagareyama; Nobuhisa Kasagima, Inashiki, all of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/555,904
(22) PCT Filed: Dec. 3, 1998
(86) PCT No.: PCT/JP98/05461
  § 371 Date: Jun. 5, 2000
  § 102(e) Date: Jun. 5, 2000
(87) PCT Pub. No.: WO99/27857
  PCT Pub. Date: Jun. 10, 1999

(30) Foreign Application Priority Data

Dec. 4, 1997 (JP) ............................................. 9-333837

(51) Int. Cl.⁷ .............................................. G01N 23/00
(52) U.S. Cl. ........................................... 378/24; 378/17
(58) Field of Search ............................... 378/24, 17, 20

(56) References Cited

U.S. PATENT DOCUMENTS 4,600,998 A * 7/1986 Huet ............................ 378/20
4,975,934 A * 12/1990 Sauerwein et al. ........... 378/20

* cited by examiner

Primary Examiner—Craig E. Church
(74) Attorney, Agent, or Firm—Antonelli, Terry, Stout & Kraus, LLP

(57) ABSTRACT

Between an X-ray generating system and an X-ray image detecting system arranged opposite to the X-ray generating system, an examination object supporting system is arranged and contains a straight movement table provided on a rotary table supported by a rotary table supporting member, and an examination object supporting member for supporting the examination object under either a standing position or a sitting position on the straight movement table. While the examination object is rotated by the rotary table, the examination object is continuously moved (reciprocating movement) by the straight movement table along a direction parallel to the rotation plane, and X-ray images of the examination object are acquired along a plurality of directions during both the rotating operation and the moving operation. As a result, both an X-ray tomographic image and a three-dimensional image (stereoscopic image) of a wider area than a viewing field of an X-ray I.I. can be acquired. Since the viewing fields of the X-ray tomographic image and of the 3-dimensional image can be employed, both diagnostic performance and also a diagnostic efficiency with respect to a large organ such as a lung can be improved.

19 Claims, 12 Drawing Sheets

(a) TOP VIEW (b) FRONT VIEW (a) $V_r$ (b) $\alpha$ (c) $S$ (d) $V_\ell$ (a)

(b)

(c)

(a)

(b)

(a)

(b)

X-RAY EXAMINATION APPARATUS AND IMAGING METHOD OF X-RAY IMAGE

TECHNICAL FIELD

The present invention is related to an X-ray examination apparatus and an imaging method of an X-ray image. More specifically, the present invention is a directed to a technique for reconstructing either a tomographic image (tomogram) or a three-dimensional image of a measuring object larger than a viewing field angle of an X-ray detector from such a X-ray image produced by imaging the measuring object while such a measuring object is rotated, and is arranged between an X-ray source and the X-ray detector.

BACKGROUND ART

As a conventional X-ray examination apparatus, there is such an X-ray CT apparatus (X-ray tomographic imaging apparatus) by which while both an X-ray source and an X-ray detector where detecting elements are arranged in one dimensional manner are rotated around an examination object by 1 rotation, a rotary imaging operation is carried out so as to acquire a distribution of X-ray absorption coefficients within the examination object as a tomographic image. Also, a s a method for acquiring a 3-dimensional image by an X-ray CT apparatus, there is a spiral scanning method in which while an examination object is continuously moved along a direction perpendicular to a rotation plane, rotary imaging operation is carried out plural times.

As a method for acquiring a distribution of X-ray absorption coefficients as a three-dimensional image, there is a cone-beam CT apparatus by which while both an X-ray source and a 2-dimensional X-ray image detector are rotated around an examination object by 1 rotation, imaging operation is carried out and a 3-dimensional image reconstruction is carried out from the acquired rotary imaging data. In such a cone-beam CT apparatus, it is generally known that a viewing angle of a cross-tomographic plane is limited by a viewing angle of a 2-dimensional X-ray image detector. Various research works about such cone-beam CT apparatuses have be potentially carried out. That is, these cone-beam CT apparatuses are capable of acquiring the 3-dimensional images having the larger viewing field angles than the viewing field of the 2-dimensional X-ray detector from the two-dimensional images which are imaged by the two-dimensional X-ray detector whose viewing field is limited.

The cone-beam CT apparatus capable of enlarging the viewing field is disclosed in, for example, JP-A-8-117220 (simply referred to as a "publication 1" hereinafter), and "SPIE Medical Imaging", pages 349 to 357 in 1997 (will be simply referred to as a "publication 2" hereinafter). In the cone-beam CT apparatus described in the publication 2, while both the X-ray source and the X-ray image detector are rotated around the examination object by two rotations, namely the normal rotation and the reverse rotation. While the examination object is reciprocated along the direction parallel to the rotation plane in the same time period as the rotation time period, the rotary X-ray imaging operation is carried out 2 times so as to acquire the three-dimensional image having the larger viewing angle than the viewing field of the two-dimensional X-ray detector from the two-dimensional image.

There are various sorts of apparatuses in which while both X-ray sources and X-ray image detectors are fixed and also examination objects such as various sorts of materials and air line baggages are rotated, rotary imaging operations are carried out.

DISCLOSURE OF THE INVENTION

Generally speaking, in the spiral scanning method, very long measurement time is required so as to make the resolution along the direction perpendicular to the rotation plane equal to the resolution within the rotation plane. As a result, the resolution along the direction perpendicular to the rotation plane would be lowered, as compared with the resolution within the rotation plane. In the cone-beam CT apparatus, the 3-dimensional image data is obtained only by performing the rotary imaging operation for one rotation. Moreover, the 3-dimensional image having the voxel resolution is obtained, and the size of this voxel resolution is the same as that within the rotation plane along the direction perpendicular to the rotation plane. As a consequence, this spiral scanning method is featured by that the true 3-dimensional imaging operation can be carried out.

The inventors of the present invention could find out the below-mentioned problems after considering the conventional techniques. Nowadays, X-ray CT apparatuses and the like are utilized not only as specific-purpose apparatuses, but also as usual-purpose examination apparatuses. However, since the conventional X-ray CT apparatuses and the like are directed to examine seriously-injured objects under examination, these objects under examination generally lie down as body attitudes. On the other hand, while performing routine diagnoses with respect to respiratory system organs such as a lung, circulatory system organs such as a blood vessel, and skeleton such as a backbone and pelvis, it is very important to image 3-dimensional images having large viewing fields as well as high resolution under such a body attitude condition that objects under examination is diagnosed under standing position, or sitting condition, namely daily natural attitude conditions in order to diagnose patients conditions. A need is made of developing such an X-ray CT apparatus for realizing a rotary imaging operation in which a rotation axis is located perpendicular to the horizontal plane in order that the object under examination is imaged under standing position, or sitting position.

In the case that the conventional X-ray apparatus, or the conventional cone-beam CT apparatus is knocked over so as to realize the rotary imaging operation, there is a first problem that a very wide floor area is required so as to install the gantry. Furthermore, in order to achieve such a purpose capable of improving resolution of an imaged image, a distance between an X-ray source and a detector cannot be changed over a wide range, resulting in a second problem. As a method of solving this second problem, for instance, there is an X-ray baggage examination (checking) apparatus used to check a baggage and the like. This X-ray baggage examination apparatus is arranged by an X-ray source, a detector arranged opposite to this X-ray source, and a rotation apparatus arranged in such a manner that a rotation axis is located on a straight line for connecting the X-ray source and the detector. While an examination object is set on the rotation apparatus, X-ray images of the examination object are imaged along a plurality of directions.

However, the imaging method of the X-ray baggage examination apparatus owns similar problems to those disclosed in the publication 1 and the publication 2. In other words, there is a third problem. That is, since the viewing field of the 2-dimensional detector is narrow, the sufficiently wide imaging viewing field cannot be secured when such a large body portion as a lung is imaged. As a result, the organ such as the lung cannot be acquired as a single reconstructed image.

On the other hand, as the 2-dimensional X-ray image detector used in the cone-beam CT apparatus, the following combined detectors may be employed, for instance, a combination between a television camera and an X-ray image intensifier (simply referred to as an "X-ray I.I." hereinafter) for converting an X-ray into an optical image, another combination between a fluorescent plate and a television camera, an another combination between a fluorescent plate and a plane sensor constructed of a 2-dimensional array made of amorphous silicon photodiodes and TFT elements. Generally speaking, these 2-dimensional X-ray image detectors own such a problem that an image quality of a reconstructed image is deteriorated, as compared with the 1-dimensional array detector used in the X-ray CT apparatus.

One of various reasons why the image quality of the reconstructed image is deteriorated is given as follows. That is to say, the sensitivities for the respective elements cannot be precisely corrected due to the sensitivity of the 2-dimensional X-ray image detector and the temperature characteristic of the noise level, so that the ring artifact is increased in the reconstructed image. Another reason as to the deterioration of the reconstructed image is given as follows: In the television camera and the photosensor such as the photodiode, which constitute the 2-dimensional X-ray image detector, the read time of one image becomes longer than the signal reading time in the 1-dimensional array detector used i the X-ray CT apparatus. As a result, a total projection number of the rotary imaging operations within 1 rotation is reduced, and thus, the radial artifact occurred in the reconstructed image is increased.

An object of the present invention is to provide such a technique capable of imaging an X-ray fluoroscopic image, an X-ray imaging image, or an X-ray tomographic image under either a standing position or a sitting position, and furthermore, capable of enlarging viewing fields of these images. Another object of the present invention is to provide such a technique capable of enlarging a viewing field of a 3-dimensional image (stereoscopic image) which is imaged under either a standing position or a sitting position; another technique capable of reducing an installation area of an X-ray examination apparatus; another technique capable of acquiring a stereoscopic image having a high image quality, which is imaged under with a standing position or a sitting position; another technique capable of reducing a load given to an examination object; another technique capable of shortening time required to execute an imaging operation; another technique capable of reducing a ring artifact; and a further technique capable of reducing a streek artifact caused by limiting a total projection number.

The objects and other novel features of the present invention may become apparent from the detailed description of the present specification, and the accompanying drawings. The typical invention disclosed therein will now be briefly explained as follows:

(1) An X-ray examination apparatus, according to the present invention, is comprised of: X-ray generating means for irradiating either a cone-shaped X-ray or a pyramid-shaped X-ray; imaging means arranged at a position opposite to said X-ray generating means, for imaging an X-ray image of an examination object; supporting means for supporting the examination object; rotating means for rotating the supporting means; and moving means for moving the supporting means along a direction parallel to a rotation plane of the rotating means; wherein: while the examination object is rotated, the position of said examination object is moved along the direction parallel to the rotation plane, and the X-ray image of the examination object is imaged during the rotating operation and the moving operation; and an X-ray fluoroscopic image, an X-ray imaging image, an X-ray tomographic image, and/or an X-ray 3-dimensional image of the examination object are produced from the X-ray images of the examination object, which are imaged along a plurality of directions, and then the X-ray fluoroscopic image, the X-ray imaging image, the X-ray tomographic image, and/or the X-ray 3-dimensional image are displayed.

(2) An imaging method of an X-ray image, according to the present invention, is comprised of: a step in which while an examination object is rotated on a straight line for connecting a focal point of an X-ray tube and a center of an X-ray detector positioned opposite to the X-ray tube, the examination object is moved in a direction parallel to and/or perpendicular to a rotation plane in synchronism with a rotation period, and an X-ray image of the examination object is imaged along a plurality of directions during the rotating operation and the moving operation of the examination object; a step for producing an X-ray fluoroscopic image, an X-ray imaging image, an X-ray tomographic image, and/or an X-ray 3-dimensional image; and a step for displaying the X-ray fluoroscopic image, the X-ray imaging image, the X-ray tomographic image, and/or the X-ray 3-dimensional image.

In accordance with the items (1) and (2), in such a case that the X-ray images of the examination object are acquired along a plurality of directions, the examination object supporting system is arranged between the X-ray generating means and the imaging means arranged opposite to the X-ray generating means. This examination object supporting system is constituted by the rotary means, the moving means, and the supporting means for supporting the examination object under standing position, or the sitting position. While the examination object is rotated by the rotating means, the examination object is continuously moved (reciprocation movement) by the moving means along the direction parallel to and/or perpendicular to the rotation plane, the X-ray image is imaged during the moving operation and the rotating operation. As a consequence, both the X-ray tomographic image and the 3-dimensional image (stereoscopic image) can be obtained which own the wider areas than the viewing field of the imaging means.

In other words, since the viewing fields of the X-ray tomographic image and the 3-dimensional image can be enlarged, the diagnostic performance and the diagnostic efficiency with respect to the large organ such as the lung can be improved. Also, when the X-ray images of the examination object are acquired along the plural directions, since both the X-ray generating means and the imaging means arranged opposite to the X-ray generating means are no longer rotated, the installation area of the apparatus can be reduced.

BEST MODE FOR CARRYING OUT THE INVENTION

Figure 1:
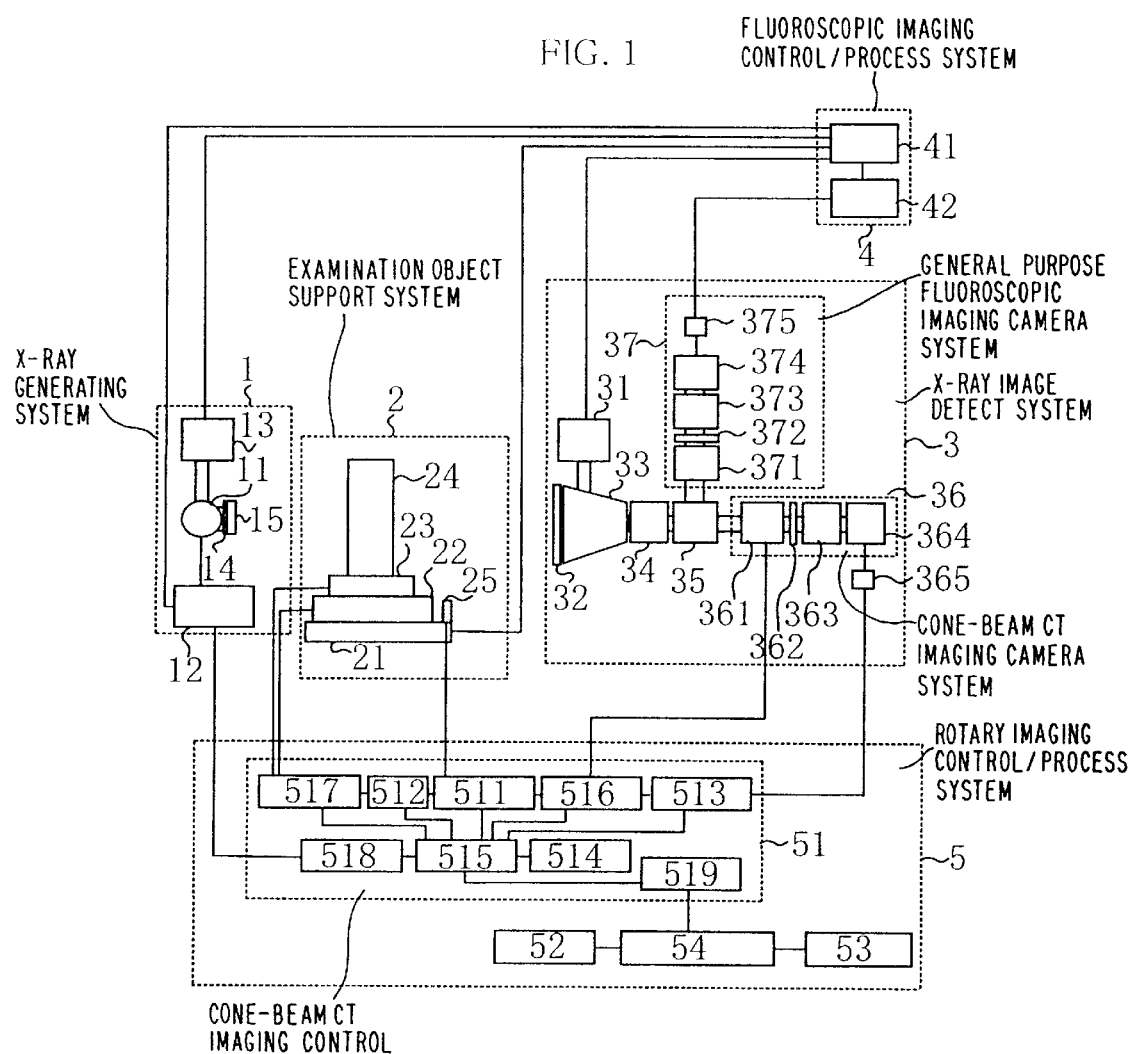
FIG. 1 is a block diagram for explaining a schematic arrangement of an X-ray examination apparatus according to an embodiment mode 1 of the present invention.

Referring now to drawings, the present invention will be described in conjunction with an embodiment mode of the present invention in detail. It should be understood that the same reference numerals shown in all of the drawings used to explain the embodiment modes of the present invention will be employed as those for denoting structural elements having the same functions, and therefore, explanations of these same structural elements are omitted.

(Embodiment Mode 1)

FIG. 1 is a block diagram for explaining a schematic arrangement of an X-ray examination apparatus according to an embodiment mode 1 of the present invention. The X-ray examination apparatus of the embodiment mode 1 is arranged by an X-ray generating system (X-ray generating means) 1, an examination object supporting system 2, an X-ray image detecting system (imaging means) 3, a fluoroscopic imaging control/processing system 4, and a rotary imaging control/processing system 5.

The fluoroscopic imaging control/processing system 4 corresponds to such a system that while controlling the X-ray generating system 1, the examination object supporting system 2, and the X-ray image detecting system 2, the general-purpose X-ray fluoroscopy and X-ray imaging operations are carried out, and after image data (X-ray image) of an examination object (human body and baggage) supported the examination object supporting system 2 is processed, the resulting image data is displayed on a display apparatus (not shown). The fluoroscopic imaging control/processing system 4 is arranged by a fluoroscopic imaging control apparatus 41, a data acquisition processing apparatus 42, and the like. These constructive apparatuses are realized by employing the well-known apparatuses.

The rotary imaging control/processing system 5 corresponds to such a system that a specific control operation to the cone-beam CT imaging of the present invention is carried out with respect to the X-ray generating system 1, the examination object supporting system 2, and the detecting system 3, which are basically controlled by the fluoroscopic imaging control/processing system 4 so as to perform the rotary imaging operation, and then the acquired image data is processed to be displayed on a display means (not shown). The rotary imaging control/processing system (period control means) 5 is arranged by a cone-beam CT imaging control apparatus 51, a controlling personal computer 52, an image reconstructing workstation 53, a data transfer interface switching device 54, and the like.

In FIG. 1, the X-ray generating system 1 is arranged by an X-ray tube for irradiating either a cone-shaped X-ray or a pyramid-shaped X-ray; an X-ray controller 12, an X-ray tube supporting member 13, an X-ray filter 14, and an X-ray collimator 15, and the like. In the embodiment mode 1, the X-ray tube supporting member 13 fixes the X-ray tube 11 on a predetermined position in a space above a floor plane on which the X-ray examination apparatus. The examination object supporting system 2 is arranged by a rotary table supporting member (supporting means) 21, a rotary table (rotating means) 22 set on the rotary table supporting member 21, a straight movement table (moving means, reciprocation moving means) 23 set on the rotary table 22, an examination object supporting member 24 set on the straight movement table 23, a rotary angle detecting mechanism 25, and the like.

The X-ray image detecting system 3 is arranged by a detector supporting member 31, an X-ray grid 32, an X-ray image intensifier (will be abbreviated to as an "X-ray I.I." hereinafter) 33, a primary lens 34, an optical distributor 35, a cone-beam CT imaging camera system 36, a general-purpose fluoroscopic imaging camera system 37, and the like. In the embodiment mode 1, the cone-beam CT imaging camera system 36 is arranged by an iris 361, an ND filter 362, a secondary lens 363, a television camera 364, a camera controller 365, and the like.

Also, the general-purpose imaging camera system 37 is arranged by an iris 371, an ND filter 372, a secondary lens 373, a television camera 374, a camera controller 375, and the like. It should be noted that in the X-ray image detecting system 3, the portions except for the detector supporting member 31 and the camera controllers 365 and 375 are held by the detector supporting member 31 on, for example, a preselected position in a space above the floor plane. For example, a distance "L" between the X-ray generating system 1 and the X-ray image detecting system 3 may be arbitrarily set by that the detector supporting member 31 is set on the movement table of the straight movement table 23, and the move direction of the detector supporting member 31 is made coincident with such a straight line which connects a focal point position of the X-ray generating system 1 and a center of the X-ray image detecting system 3. As a result, in response to an instruction issued by an examiner, the interval "L" is increased, so that the X-ray beams entered into the X-ray I.I. 33 can be approximated to more collimated X-ray beams. As a consequence, the resolution of the CT image and also the resolution of the 3-dimensional image, which are obtained by performing the reconstruction calculation, can be improved.

The cone-beam CT imaging control apparatus 51 is arranged by an interface (namely, rotary angle detecting interface 511, camera interface 513, iris interface 516, rotary table/straight movement table control interface 517, X-ray control interface 518, and data transfer interface 519), a synchronization signal generating unit 512, a frame memory 514, a digital signal processing processor (DSP) 515, and the like. The interface reads a signal sent from an apparatus connected to the control apparatus 51, or outputs a signal to each of the apparatuses. The synchronization signal generating unit 512 generates a synchronization used to establish various timing such as generating timing of an X-ray in the X-ray tube 11 based upon the rotary angle data sent out from the rotary angle detecting mechanism 25, and acquisition timing of image data in the television camera 364 in response to the rotary angle data supplied from the rotary angle detecting mechanism 25. The frame memory 514 sequentially stores thereinto X-ray images imaged by the cone-beam CT imaging camera system 36. The digital signal processing processor (DSP) 515 calculates both a width of an optimum pulse X-ray and an aperture of an iris based upon the imaged X-ray image and the imaging condition.

Figure 2:
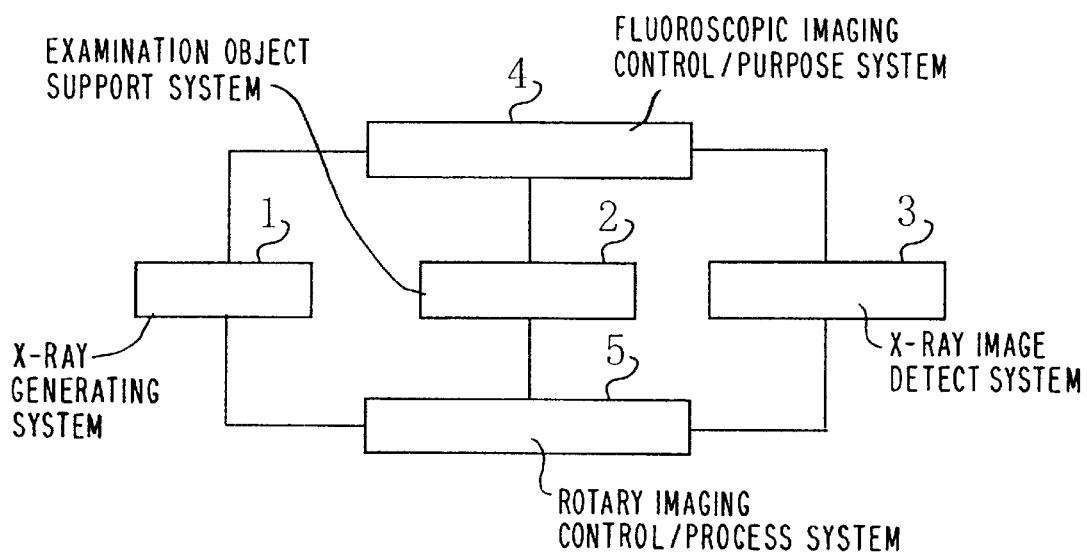
FIG. 2 is a diagram for representing the arrangement of the X-ray examination apparatus of the embodiment mode 1 by combining several structural elements with each other in large blocks.

FIG. 2 is a block diagram for representing the arrangement of the X-ray examination apparatus according to the embodiment mode 1 by combining the structural elements with each other in large blocks. The X-ray examination apparatus, according to the embodiment mode 1, is featured by owning two sets of control systems, namely, both the fluoroscopic imaging control/process system 4 and the rotary imaging control/process system 5.

In accordance with the arrangement of the X-ray examination apparatus of the embodiment mode 1, both the hardware as well as the software of the existing fluoroscopic image control/process system 4 need not be altered. The following feature may be achieved. Since both the X-ray fluoroscopic examination and the imaging operation according to the conventional technique can be executed similar to the conventional manner even after the rotary imaging control/process system 5 has been added, the function of the cone-beam CT apparatus can be additionally provided with the existing fluoroscopic/imaging apparatus within a short time and in low cost.

Referring now to FIG. 1, a description will be made of a preparation operation for a cone-beam CT imaging operation performed by the X-ray examination apparatus according to the embodiment mode 1. First, an examiner (not shown) actuates the function of the fluoroscopic imaging apparatus 41 to control the X-ray tube supporting member 13, the rotary table supporting member 21, and the detector supporting member 31. The examiner positions the X-ray tube 11 opposite to the X-ray I.I. 33 equipped with the X-ray grid 32, and also locates the examination subject supporting system 2 between the X-ray tube 11 and the X-ray grid 32, and further controls an angle of a rotary mirror provided inside the optical distributor 35 in such a manner that an output image of the x-ray I.I. 33 is focused onto the cone-beam CT television camera 364 based upon the function of the fluoroscopic imaging apparatus 41. When the examiner controls the angle of the rotary mirror, this examiner sets a switch for selecting the operation mode of the X-ray controller 12 to such a motor for accepting a command of the cone-beam CT imaging control apparatus 51.

Next, the examiner sets a basic imaging condition related to the cone-beam CT imaging operation with respect to the cone-beam CT imaging control apparatus by employing the controlling personal computer 52. When this basic imaging condition is set, the examiner performs the following selections: (1) Either a standard viewing field mode or an enlarge viewing field mode is selected. In the standard viewing field, a simple one-rotation imaging operation is carried out as an imaging sequence. In the enlarge viewing field mode, an examination object is moved on the straight movement table while executing a rotary image operation so as to enlarge both a viewing field of a tomographic image plane and a viewing field of a 3-dimensional imaging operation. (2) As an X-ray condition for irradiating an X-ray to an examination object, either a continuous X-ray mode or a pulse X-ray mode is selected. In the continuous X-ray mode, the continuous X-ray is irradiated. In the pulse X-ray mode, the pulse X-ray is irradiated. (3) As an imaging control system, either an imaging condition fix mode or an imaging condition automatic adjust mode is selected. In the imaging condition fix mode, the respective X-ray imaging operations are carried out under the same X-ray amount and the same iris aperture. In the imaging condition adjust mode, both the X-ray amount and the iris aperture are changed in conjunction with the rotation of the examination object. It should be noted that in the imaging condition automatic adjust mode by selecting the continuous X-ray made, the X-ray amount is not changed, but only the aperture of the iris is changed. In the setting condition (2), when the pulse X-ray mode is selected, since the X-ray irradiation time within each frame is shorter than that of the continuous X-ray mode, the move amount of the examination object within the X-ray irradiation time is small. As a consequence, an image blurring phenomenon caused by the movement of the examination object is decreased, and thus, the spatial resolution of the image can be improved. Also, in the imaging condition (3), when the imaging condition automatic adjust mode is selected, since each project image can be imaged by using a proper X-ray amount and a proper iris aperture, noise contained in a reconstructed image can be reduced and an S.N ratio thereof can be improved.

Next, as a typical example, assuming now that a selection is made of such a combination of the enlarge viewing field mode, the pulse X-ray mode, and the imaging condition automatic adjust mode, a setting method for setting various sorts of basic imaging conditions explained as follows:

Among the setting items related to the X-ray generating system 1, both an X-ray tube voltage and an X-ray tube current are set by using an X-ray control panel of the X-ray controller 12. Also, while using the controlling personal computer 52, an initial value of a width of a pulse X-ray is set with respect to the cone-beam CT imaging control apparatus 51. Also, while using the controlling personal computer 52, both a rotary speed (rotation velocity) of the examination object supporting system 2 and an amplitude of reciprocation straight movement are set with respect to the cone-beam CT imaging control apparatus 51. It should also be noted that the initial position of the straight movement table 23 is moved to a preselected position. Also, the straight movement of the straight movement table 23 is set by the cone-beam CT imaging control apparatuses 51 in such a manner that the positional coordinate of the straight movement table 23 is varied in a sine wave manner while time has passed.

Among the setting items related to the X-ray image detecting system 3, the viewing field mode of the X-ray I.I. 33 is set by the fluoroscopic imaging control/process system 4. All other items are set with respect to the cone-beam CT imaging control apparatus 51 by the examiner by using the controlling personal computer 52. As other setting items, there are an initial setting value of the aperture of the iris 361, a transmittance of the ND filter 362, storage time of an imaging element built in the television camera 364, a gain of an amplifier built in the television camera, a pixel number of an image outputted from the television camera, a frame rate of a image outputted from the television camera, a total number $N_r$ of acquired images during a single rotary imaging operation.

It should be understood that a total number $N_t$ of acquired images in the enlarge viewing field mode becomes two times larger than the above-explained total number $N_r$. In this embodiment mode 1, as the X-ray I.I. 33, 16-inch type X-ray image intensifier is employed, and as the viewing field mode, any one of 16 inches, 12 inches, 9 inches, and 7 inches may be set. As the television camera 364, such a CCD camera capable of outputting 1024×1024 pixels in maximum is utilized. As a combination between the pixel number of the television camera and the frame rate thereof, the following combination is the standard combination, namely 60 f (frame)/sec with respect to an output of 512×512 pixels, and 30 f/sec with respect to an output of 1024×1024 pixels. To suppress an adverse influence caused by motion of an examination object to a minimum value, a large number of projection images must be imaged within a short time period. In general, a selection is made of such a condition that a frame rate is large. On the other hand, in order to obtain a high resolution image, a selection is made of such a condition that a pixel number is large. For example, in order to perform an imaging operation capable of obtaining ultra high resolution while narrowing an imaging viewing field, the 7-inch viewing field mode may be set in the standard viewing field imaging mode, and the 1024×1024 pixel mode.

A typical gain setting value of the amplifier built in the television camera 364 corresponds to such a setting value by which an output level of an A/D converter contained in the television camera becomes a maximum level with respect to an amount of incident light when a CCD (Charge-Coupled Device) element is saturated. The dynamic range of the CCD element can be utilized by employing this typical setting value in a maximum efficiency. In this embodiment mode 1, the aperture of the iris 361 may be set within a range of 9 mm to 50 mm. In the imaging condition automatic adjust mode, since the aperture of this iris is varied in a half way while the rotary imaging operation is carried out, an initial setting value of the aperture of the iris is set to an intermediate aperture of the settable range. In the embodiment mode 1, as the ND filter 362, a liquid crystal variable ND filter is employed, and the transmittance of this liquid crystal variable ND filter may be controlled by an applied voltage. When the aperture of the iris is determined, an amount of X-rays entered into the X-ray I.I. is determined by the transmittance of the ND filter. In the case that the X-ray amount is set to a low X-ray amount so as to reduce an exposure X-ray amount of an examination object, the transmittance of the ND filter must be set to a large value. On the other hand, when the X-ray amount is set to a high X-ray amount in order to obtain a high image quality, the transmittance of the ND filter is set to a small value.

Next, a description will now be made of control operations in the viewing field enlarge mode. The rotation of the rotary table 22 is commenced at an angle just before a reference angle (namely, angle of 0) at which the rotary imaging operation is commenced, and then, the rotation speed of this rotary table 22 is reached to a constant rotation speed until this rotary table 22 passes through the reference angle. The rotation angle of the rotary table 22 may be detected by continuously monitoring a signal derived from the rotary angle detecting mechanism 25 via the rotary angle detecting interface 511.

When the rotary angle detecting interface 511 detects the reference angle, the synchronization signal generating unit 512 generates an external synchronization signal. The external synchronization signal is sent via the camera controller 365 to the television camera 364, and the CCD element of the television camera starts the storage operation in response to the external synchronization signal. Also, in response to this external synchronization signal, a width signal of a pulse X-ray is produced via the X-ray controller interface 518. The width signal of the pulse X-ray is entered into the X-ray controller 12, so that a high voltage pulse corresponding to the pulse width of the pulse signal of the pulse X-ray is generated to be inputted to the X-ray tube 11. In response to the inputted high voltage pulse, the X-ray tube 11 produces a pulse-shaped X-ray and irradiates this pulse X-ray to the examination object.

When the rotary angle detection interface 511 detects the reference angle, the rotary/straight movement table interface 517 causes the straight movement table 23 to commence the straight reciprocating movement in such a manner that the positional coordinate of the straight movement table is varied in the sine wave form in connection with the time lapse, and furthermore, when the reference angle detecting mechanism detects the reference angle, the positional coordinate of the straight movement table owns a maximum deviation from a rotation center of the rotary table 22. In the rotary/straight movement table interface 517, such a pulse train is produced to be outputted to the straight movement table 23. The pulse number of this pulse train per unit time is changed in the sine wave form in connection with the time lapse. In response to the entered pulse train, a linear motor employed in the straight movement table 23 is driven, so that the coordinate of the straight movement table 23 is changed by this drive force in the sine wave form in connection with the time elapse.

As to the X-ray emitted from the X-ray tube 11, the low energy components of this X-ray is cut by the X-ray filter 14, and the irradiation area is limited to an imaging area by the X-ray collimator 15, and thereafter the resultant X-ray is irradiated to the examination object. The X-ray which has penetrated both the examination object and the examination object supporting member 24 is attenuated by the X-ray grid 32 positioned in front of the X-ray I.I. 33 by partially shielding scattering X-rays which are scattered within the examination object. Thereafter, the attenuated X-ray is entered into the X-ray I.I. 33. A major portion of the X-ray entered into the X-ray I.I. 33 is converted into fluorescent by the input fluorescent plane of this X-ray I.I., and then this fluorescent is entered into a photo conductive plane which is positioned close to the input fluorescent plane so as to be converted into photoelectrons. The photoelectrons are accelerated inside the X-ray I.I., and then the accelerated photoelectrons are entered into the output fluorescent plane of the X-ray I.I. 33 so as to be focused thereon. The fluorescent produced by the accelerated electrons entered into the output fluorescent plane is outputted as a visual light image (X-ray image).

This visual light image is converted into parallel light by the primary lens 34, and then this parallel light is entered into the optical distributor 35. The parallel light entered into the optical distribution 35 is projected to the cone-beam CT camera system 36 by the rotary mirror of the optical distributor 35 while the cone-beam CT imaging operation is carried out. After the light amount of the parallel light entered into the cone-beam CT television camera system 36 is limited by the iris 361, the light amount thereof is adjusted by the ND filter 362 and is then focused on the imaging element of the television camera 364 by the secondary lens 363, so that electron charges are accumulated on the imaging element. A total number of accumulated electron charges are increased in a time period during which the pulse X-ray is continued, and in a time period which is determined by a fluorescent attenuation time constant of fluorescent materials of the output fluorescent plane of the X-ray I.I. 33. When a predetermined accumulation time has passed, the change accumulation is accomplished, and the image information is read out in the order of pixels by the effect of this CCD element, and then the read image information is converted into the voltage signal which will be then amplified by the amplifier. The amplified image signal is A/D-converted into the digital image signal by the A/D converter. Thus, this digital images signal is outputted from the television camera 364. The image information (x-ray image) outputted from the television camera is stored via the camera controller 365 and the camera interface 513 into the frame memory 514.

Figure 3:
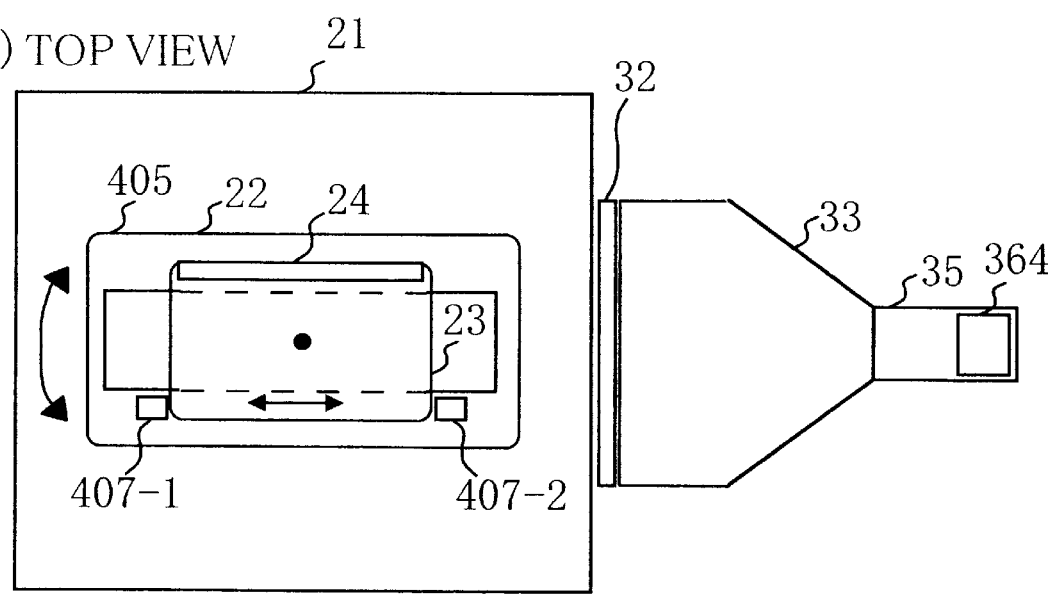
FIG. 3 is explanatory diagram for explaining more in detail the structure of the examination object supporting system of the embodiment mode 1.
Figure 3:
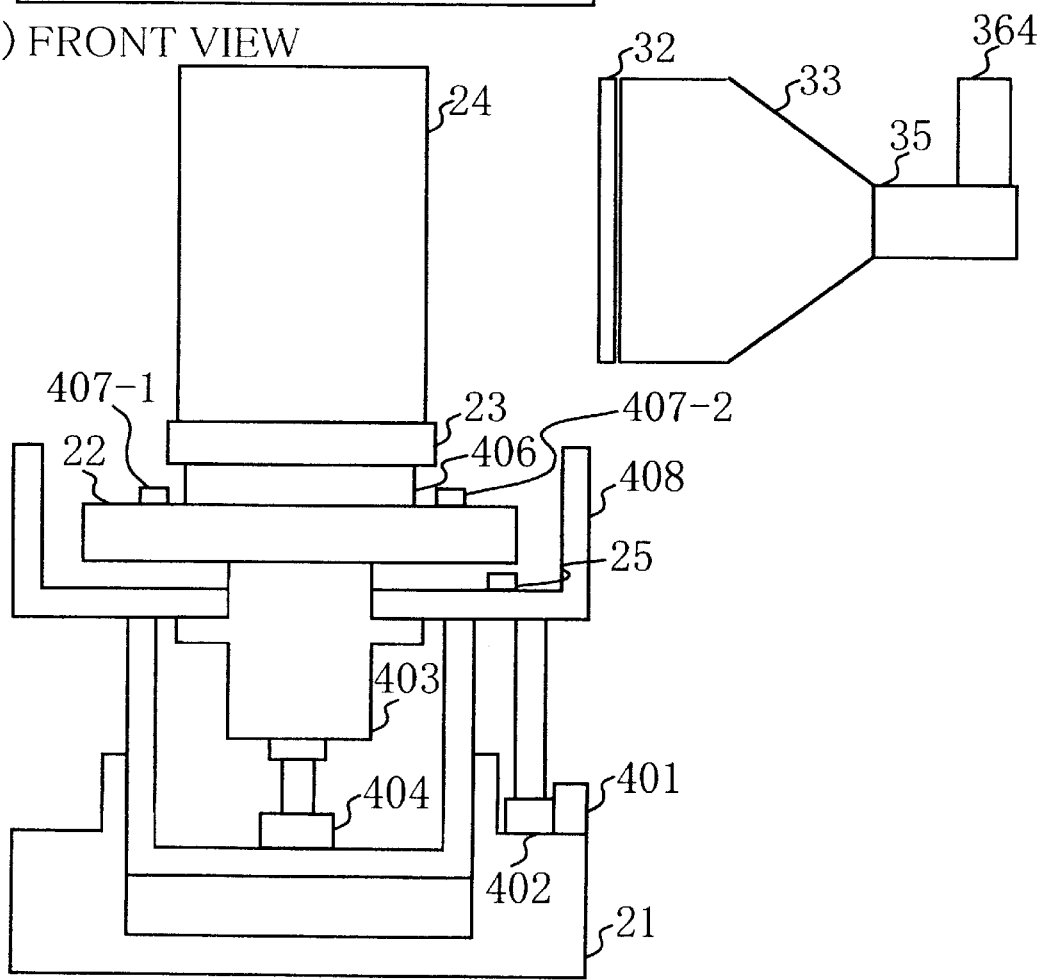

FIG. 3 is an explanatory diagram for explaining the arrangement of the examination object supporting system 2 according to the embodiment mode 1 more in detail. That is, FIG. 3(a) is an upper view of this examination object supporting system 2, and FIG. 3(b) is a front view thereof. To the rotary table supporting system 2, several sets of structural elements are attached which are omitted from the arrangement of FIG. 1. That is, the rotary supporting system 2 contains an up/down (lift) movement table 408 and a motor 401 for adjusting a height of the up/down movement table above the rotary table supporting member 21. The height of the rotary table 22 is adjusted along the upper/lower directions by the function of a smoothy jack 402 coupled to the height adjusting motor 401. The rotary table 22 is rotated by a rotary table motor 403. This rotary table motor 403 is, for example, a 5-phase pulse motor. The electric connection conditions to the rotary table motor 403 are maintained by a rotary connector 404 at all of the rotary angles. A straight movement mechanism 405 for moving the straight movement table 23 is installed above the rotary table 22. The straight movement mechanism 405 moves the straight movement table 22 by the function of a pulse linear motor 406. The rotary angle detecting mechanism 25 for detecting the rotary angle of the rotary table 22 is mounted on the rotary table supporting member 21. Two sets of straight movement limiters 407-1 and 407-2 for limiting the movement position of the straight movement table 23 are mounted on the rotary table 22.

The examination object supporting system of the embodiment mode 1 owns such a feature that the height of the examination object can be changed in an equi-speed in the rotary imaging operation. While the rotary imaging operation is carried out plural times, since the height of the examination object is changed in the equi-speed, the spiral CT scanning operation of the examination object may be performed. In such a case that the spiral scanning operation is carried out by employing a two-dimensional detector, a viewing field of a three-dimensional imaging operation can be enlarged along a rotation axial direction, as compared with that of a simple rotary imaging operation. As a result, a viewing field of a three-dimensional imaging operation can be enlarged along a body axial direction with respect to either an examination object at a standing position or an examination object at a sitting position. Also, the X-ray beams which are dispersed along the rotation axial direction are collimated by the collimator, the spiral scanning operation is carried out, and the area of the examination object which is irradiated by the X-ray can be reduced. As a consequence, the mixture of the scattered rays can be reduced. As a consequence, the positional dependency characteristic of the X-ray absorption coefficient which is calculated by reconstructing the image can be reduced, and the correctness of the value of the X-ray absorption coefficient can be improved.

Figure 4:
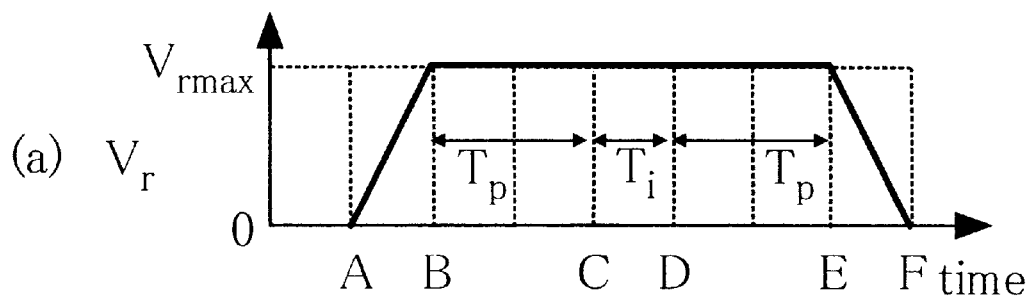
FIG. 4 is a time chart for describing a rotary imaging operation capable of enlarging a viewing field in the X-ray examination apparatus of the embodiment mode 1.
Figure 4:
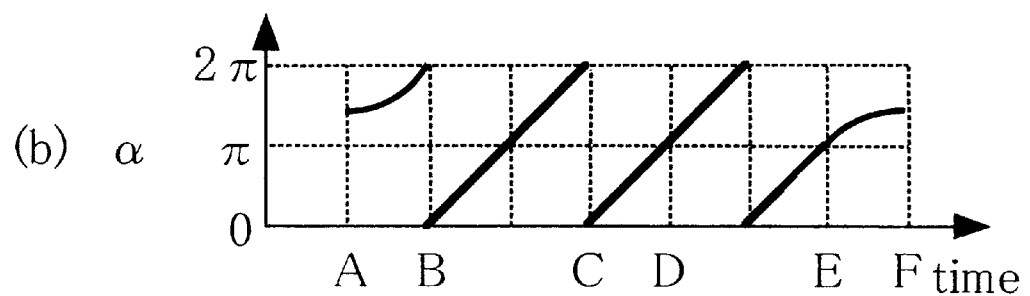
Figure 4:
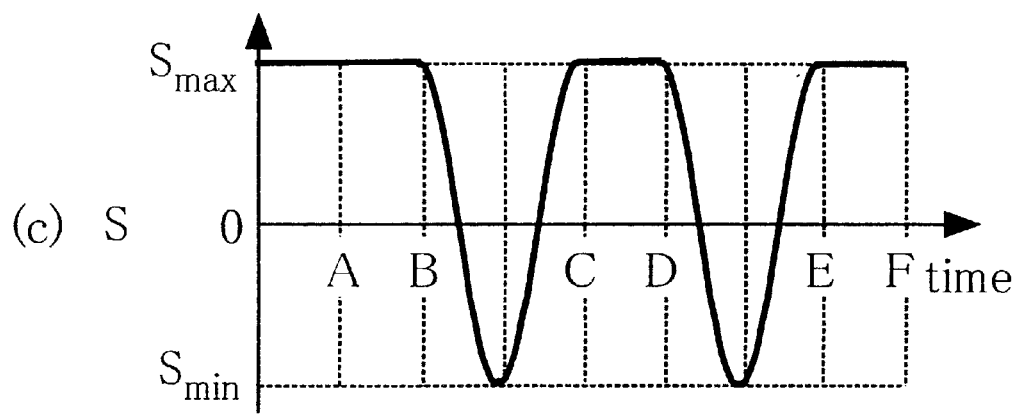
Figure 4:
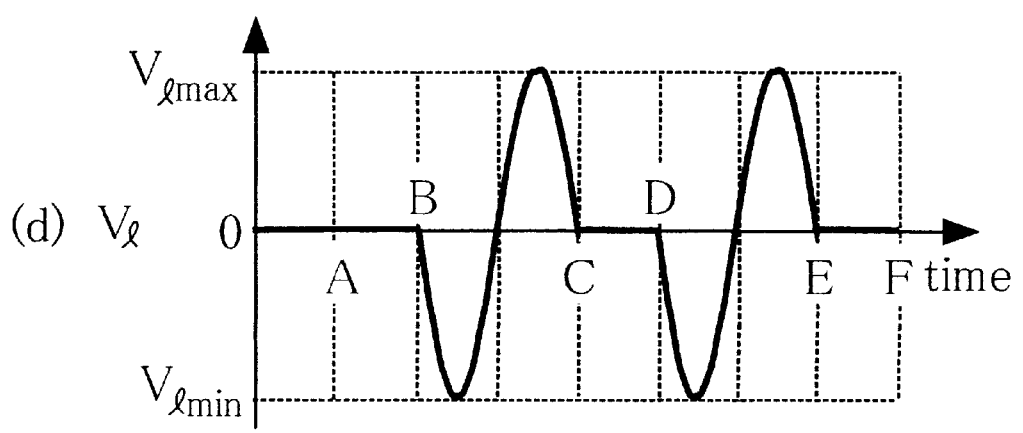

FIG. 4 represents an overall time chart (imaging sequence) of a rotary imaging operation in the enlarge viewing field mode executed in the X-ray examination apparatus according to the embodiment mode 1. FIG. 4(a) shows a time change of a rotation speed "$V_r$" (rad/sec), FIG. 4(b) represents a time change of a rotary angle "$\alpha$" (rad), FIG. 4(c) indicates a time change for representing a time change of a position "S" of the straight movement table, FIG. 4(d) shows a time change of a speed (velocity) "$V_l$" of the straight movement table. Subsequently, operations of the X-ray examination apparatus according to the embodiment mode 1 will now be explained with reference to FIG. 4. It should be noted that an abscissa shows a time axis; symbol "A" indicates a time instant when a rotation of an examination object is commenced; symbol "B" denotes a time instant when a rotary imaging operation of a first rotation is commenced; symbol "C" represents a time instant when the rotation of the examination object is ended; symbol "D" shows a time instant when a rotary imaging operation of a second rotation is commenced; symbol "E" represents a time instant when the rotation of the examination object is ended; and symbol "F" shows a time instant when the rotation of the examination object is accomplished. As a consequence, a time period "AB" shows a rotation accelerating time period before commencing the rotary imaging operation; a time period "BC" represents a time period during which the rotary imaging operation of the first rotation is executed, namely a length "$T_p$"; a time period "CD" indicates a time period of an interval between the rotary imaging operation of the first rotation and the rotary imaging operation of the second rotation, namely a length "$T_i$"; a time period "DE" represents a time period during which the rotary imaging operation of the second rotation is executed, namely a length "$T_p$"; and a time period "EF" shows a rotation decelerating time period after the rotary imaging operation is ended.

In the embodiment mode 1, the rotary imaging operation is commenced at such a time instant when the rotary angle becomes a reference value (zero). Concretely speaking, in accordance with the method for generating the synchronization signal used to control the imaging timing, there is a slight difference between a time instant when the rotary angle becomes zero and another time instant when an acquisition of a first image is commenced. In such a case that the imaging timing control operation is carried out by utilizing an internal synchronization signal of a camera, the time instant "B" when the rotary imaging operation is commenced is not equal to such a time instant when the rotary angle becomes zero, but equal to such a time instant when a first internal synchronization signal appears after the rotary angle becomes zero. On the other hand, in the case that the synchronization signal generating unit 512 generates the external synchronization signal from the angle zero signal, and then the imaging timing control operation is carried out by utilizing this external synchronization signal, the time instant "B" when the rotary imaging operation is commenced may be made coincident with the time instant when the rotary angle becomes zero.

FIG. 4(a) is a diagram for showing a change in the rotation speed $V_r$ of the rotary table in the unit of radian/second (rad/sec). FIG. 4(b) is a diagram for indicating a time change of the rotary angle "$\alpha$" of the rotary table. FIG. 4(c) is a diagram for showing the positional coordinate S of the straight movement table, while the reference movement direction of the straight movement table is set as a positive direction. FIG. 4(d) is a diagram for showing the move speed "$V_l$" of the straight movement table. As indicated in FIG. 4(a), in the X-ray examination apparatus according to the embodiment mode 1, the following feature is achieved. That is, even in the time period "BE", namely even in the interval defined between the rotary imaging operation of the first rotation and the rotary imaging operation of the second rotation, the rotary table is rotated at the same rotation speed "$V_{rmax}$" as that of the rotary imaging operation.

As indicated in FIG. 4(b), since the rotary angle "$\alpha$" of the rotary table 22 passes through zero at the time instant of the point B and is rotated at the same rotation speed during the time period BE, the change rate of the rotary angle becomes constant. As a result, when the time instant B is recognized as an origin of time, a rotary angle at arbitrary time "t" within the time period BC is expressed by the following formula (1). In the X-ray examination apparatus of the embodiment mode 1, the following feature is achieved. That is, while a time instant when the rotary angle "$\alpha$" becomes $\pi$ radians is set as a point "D", the rotary imaging operation of the second rotation is commenced. As a consequence, a relationship between $T_i$ and $T_p$ is expressed by the following formula (2). It should be noted that the change rate of the rotary angle is gradually increased during the rotation acceleration period AB, whereas the change rate of the rotary angle is gradually decreased during the rotation deceleration period EF:

$$\alpha = 2\pi \cdot t / T_p \quad \text{(formula 1)}$$

$$T_i = T_p / 2 \quad \text{(formula 2)}$$

As indicated in FIG. 4(c), the X-ray examination apparatus of the embodiment mode 1 is featured as follows: Within the time period BC and the time period DE, namely, within the imaging time periods of the first rotation and the second rotation, the position of the straight movement table 23 is controlled in accordance with the same cosine curve. Also, within the time periods AB, CD, and EF, namely within the acceleration time period, the imaging interval, and the deceleration time period, the position of the straight movement table 23 is fixed to a value "$S_{max}$" of the amplitude which is preset by the examiner. On the other hand, the position "S" of the straight movement table 23 within the time period BC is expressed by the following formula (3). It should also be noted that the position "S" of the straight movement table 23 is equal to a maximum deviation $S_{max}$, namely constant within the time period CD. Also, it should be noted that in the example shown in FIG. 4(c), $S_{min} = -S_{max}$:

$$S = S_{max} \cdot \cos(2\pi \cdot t / T_p) \quad \text{(formula 3)}$$

As shown in FIG. 4(d), the X-ray examination apparatus of the embodiment mode 1 is featured as follows: Within the time period BC and the time period DE, the speed $V_l$ of the straight movement table draws the same sine curve, and is equal to zero within all time periods other than the time period BC and the time period DE. The speed $V_l$ of the straight movement table within the time period BC is expressed by the following (4). As a consequence, the speed "$V_{lmax}$" shown in FIG. 4(d) is given by the formula (5). It should also be understood that in the example of FIG. 4(d), $V_{min} = -V_{max}$.

$$V_l = dS/dt = -2\pi \cdot S_{max} \cdot \sin(2\pi \cdot t / T_p) / T_p \quad \text{(formula 4)}$$

$$V_{lmax} = 2\pi \cdot S_{max} / T_p \quad \text{(formula 5)}$$

In such a case that while the examination object is rotated, the examination object is image in the enlarge viewing field mode by employing the straight movement table (examination object movement table) 23 capable of controlling the movement of the examination object on the rotation plane independent from the rotation, a description will now be made of reasonable ideas as to the structure of the straight movement table on the rotary table shown in FIG. 1, and the sequential control of the table movement shown in FIG. 4.

When the examination object is imaged in the enlarge viewing field mode, a center of this examination object, namely a gravity center thereof is made positionally coincident with the center of the examination object movement table, and the viewing field is enlarged in the equal sizes along both the right/left directions. Such an imaging model is acceptable. With respect to this imaging model, the reasonal movement control may be conducted from the below-mentioned two conditions: The condition (1); an absolute value of an acceleration speed (namely absolute value of acceleration speed vector) which is applied to the center of the examination object movement table with respect to the stationary coordinate system is constant after the rotary imaging operation is commenced, and until the imaging operation involving the imaging interval is ended. The condition (2); a deviation angle (declination) of an acceleration vector of the examination object movement table with respect to the stationary coordinate system is changed in a continuous manner in connection with the time elapse.

Figure 5:
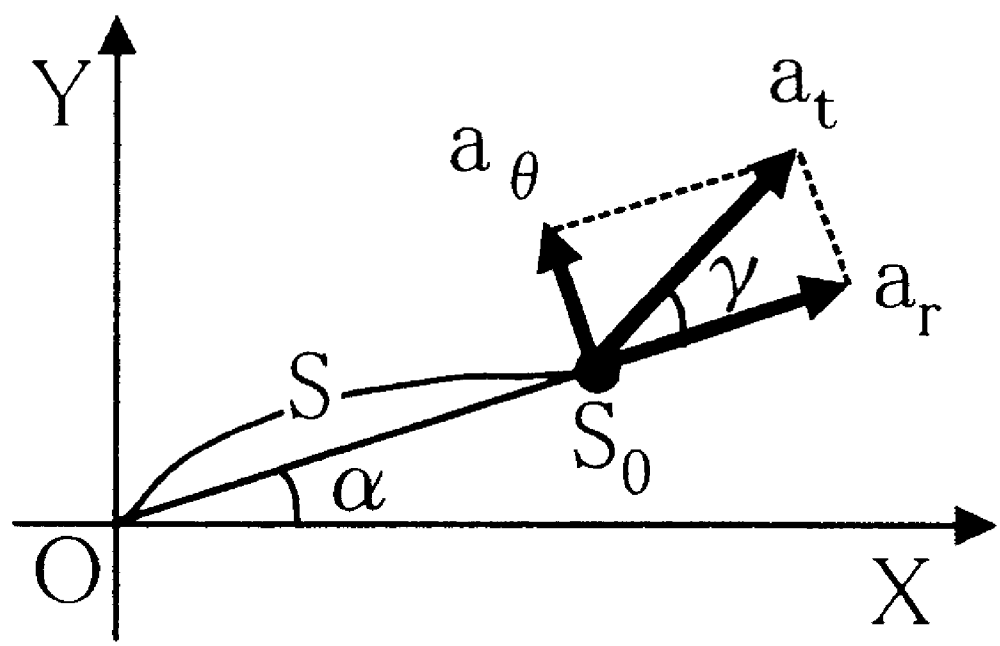
FIG. 5 is a diagram for schematically representing a center position of an examination object movement table within a stationary coordinate system at arbitrary time during the rotary imaging operation.

FIG. 5 is a diagram for schematically representing a center position of an examination object movement table within a stationary coordinate system at arbitrary time during the rotary imaging operation. In FIG. 5, a point "O" shows a position of a rotation center of the examination object rotary table fixed in the stationary coordinate system, and corresponds to a coordinate origin of the stationary coordinate system. Both an X axis and a Y axis correspond to directions within a coordinate system fixed to the stationary coordinate system. These directions are intersected with, and are positioned in parallel to a straight line for connecting a focal point of the X-ray tube and a center of the detector. Also, a point "$S_0$" indicates a position of the center of the examination object movement table at time "t" during the rotary imaging operation; symbol "$\alpha$" shows a rotary angle of the point $S_0$ at the time "t" with respect to the X axis; symbol "S" represents a distance between the point O and the point $S_0$; a vector "$a_t$" represents an acceleration vector of the point $S_0$; a vector "$a_r$" and another vector "$a_\theta$" shows acceleration vector components of the vector "$a_t$" which are distributed along a move radial direction of a rotation (radial direction), and a direction perpendicular to this move radial direction (tangential direction), respectively. The condition (1) is expressed as a problem for determining S capable of satisfying the above-explained formula (6) as a function of the time "t". It should be noted that symbol "K" is a constant irrespective of the time "t" in the formula (6). Generally speaking, in a polar coordinate system, acceleration vector components of a positions (r, $\theta$) are expressed by the below-mentioned formula (7) and formula (8), respectively. Assuming now that the movement table along the radial direction is employed as a mechanism which is independently provided with the rotary table, since the rotation speed can be made constant, the rotation speed "$\beta$" can be expressed by the following formula (9) if the rotations speed is expressed by "$\beta$". When the formula (7), the formula (8), and the formula (9) are substituted for the formula (6), and furthermore, "r" is replaced by "S", the resulting formula (10) may be obtained. A solution of the differential equation of the formula (10) becomes a solution of the movement along the radial direction. It should also be noted that a boundary condition becomes the below-mentioned formulae (11) to (14):

$$|a_t|^2 = |a_r|^2 + |a_\theta|^2 = k^2 \quad \text{(formula 6)}$$

$$a_r = (d^2r/dt^2) - r(d\theta/dt)^2 \quad \text{(formula 7)}$$

$$a_\theta = 2(dr/dt)\cdot(d\theta/dt) + r\cdot(d^2\theta/dt^2) \quad \text{(formula 8)}$$

$$d\theta/dt = 2\pi/T_p = \beta \quad \text{(formula 9)}$$

$$\{(d^2S/dt^2) - \beta^2 \cdot S\}^2 + \{2\beta\cdot(dS/dt)\}^2 = k^2 \quad \text{(formula 10)}$$

$$0 \leq t \leq T_p \quad \text{(formula 11)}$$

$$[S]_{t=0} = [S]_{t=T_p} = S_{max} \quad \text{(formula 12)}$$

$$[S]_{t=T_p/2} = -S_{max} \quad \text{(formula 13)}$$

$$[dS/dt]_{t=0} = [dS/dt]_{t=T_p/2} = [dS/dt]_{t=T_p} \quad \text{(formula 14)}$$

Now, if the solution of the formula (10) is set as the following formula (15), then this formula (10) is extended to be solved, so that the below-mentioned formula (16) is given. In the formula (15), symbol "Σ" indicates a summation of n=1 to n=∞.

$$S = (a_0/2) + \Sigma a_n \cdot \cos(n\cdot\beta\cdot t) + \Sigma b_n \cdot \sin(n\cdot\beta\cdot t) \quad \text{(formula 15)}$$

$$S = S_{max} \cdot \cos(\beta\cdot t) \quad \text{(formula 16)}$$

In other words, it can be proved that since the same result in the case of the time period BC shown in FIG. 4(c) is obtained, the control operation of the formula (3) is the optimum control operation.

An absolute value of an acceleration speed is given as the following formula (17). Based upon this formula (17), the absolute value of the synthesized acceleration speed vector is determined only by the amplitude of the straight movement and the rotation speed, and does not depend upon time:

$$k = 2\beta^2 \cdot S_{max} \quad \text{(formula 17)}$$

Next, when an argument angle arg ($a_t$) of the synthesized acceleration vector is calculated, the following formula (18) is obtained:

$$arg(a_t) = 2\pi\cdot t/T_p + \tan^{-1}\{|a_\theta|/|a_r|\} = 4\pi\cdot t/T_p \quad \text{(formula 18)}$$

The argument angle of the acceleration speed angle of the examination object movement table with respect to the stationary coordinate system is continuously changed in connection with the time lapse. In other words, since the direction of the acceleration speed vector of the center of the examination object movement table (gravity center of examination object) is changed in a smooth manner in connection with the time elapse, it can be judged that the lowest load is given to the examination object. As a result, the control operation expressed in the formula (16) is the reasonable control operation in view of the lowest load given to an object under examination. Within the time period DE, the same control operation is carried out with respect to that of the time period BC while only the phase of the rotary angle is different from that of the time period BC. Similar to the control shown in the formula (3), it can be judged that this control operation gives the lowest load to the examination object.

Figure 6:
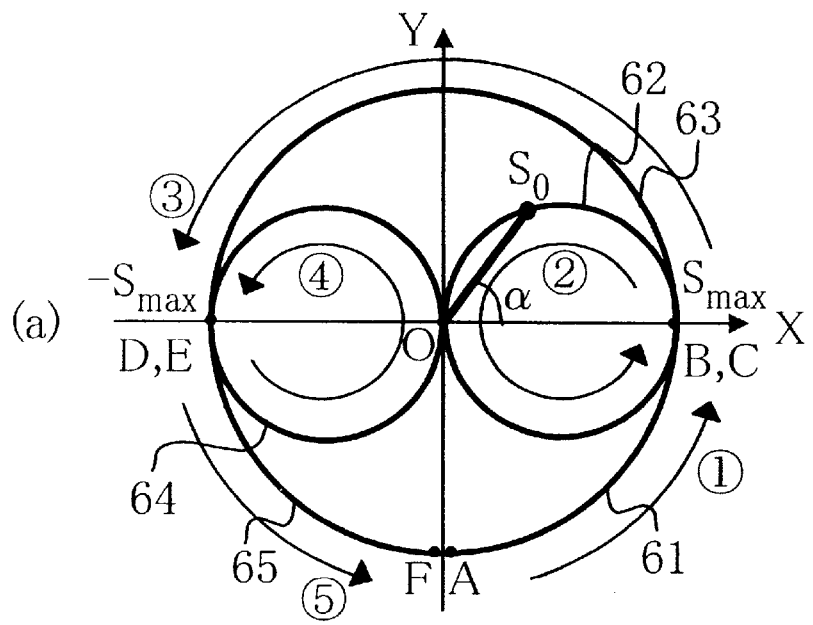
FIG. 6 is a diagram for indicating a trail illustrated by a center of a straight movement table by the sequence shown in FIG. 4.
Figure 6:
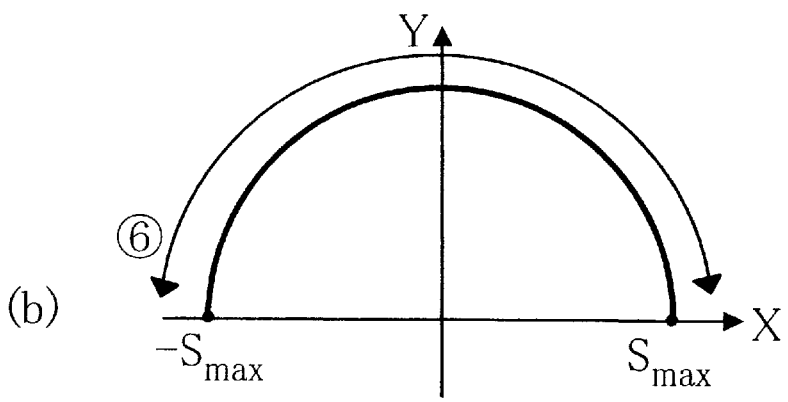
Figure 6:
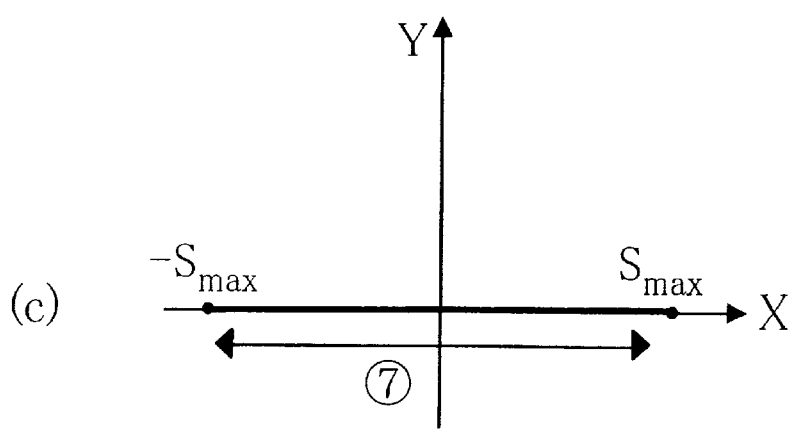

A trail of the center of the straight movement table based upon the sequence shown in FIG. 4 is represented in FIG. 6(a), FIG. 6(b), and FIG. 6(c). In FIG. 6(a), a ¼ circle of the fourth quadrant indicates a trail ① during the rotation acceleration of the time period AB within the control sequence of FIG. 4; a circle 62 indicates a trail ② (2 rounds) during the rotary imaging operation within the time period BC. A half circle 63 of both the first quadrant and the second quadrant represents a trail ③ in the imaging operation space of the time period CD; a circle 64 indicates a trail ④ (2 rounds) during the rotary imaging operation of the second rotation within the time period DE; and also a ¼ circle of the third quadrant shows a trail ⑤ during the rotation deceleration operation of the time period EF.

The center ($S_0$) of the straight movement table, namely the gravity center of the examination object is moved in the equi-speed movement over the circular orbit ((①) to (⑤)) shown in FIG. 6(a). The change in the gravity center of the examination object along the move direction is smooth, and the load given to the examination object is small, so that lowering of the spatial resolution caused by the movement can be prevented. As previously described, the foregoing description can prove that the sequence shown in FIG. 4 corresponds to the theoretically optimum system.

The numeral values employed in a concrete example as to the movement condition of the examination object movement table indicated in FIG. 4 and FIG. 6(a) are described as follows: $S_{max}$=50 (mm), $S_{min}$=−50 (mm), $T_p$=2π (sec), $T_i$=π (sec), β=1 (rad/sec), $V_{lmax}$=50 (mm/sec), $V_{lmin}$=−50 (mm/sec), $V_{rmax}$=1.3 (rad/sec), k=100 ((rad/sec)$^2$mm).

Next, a description will now be made of a technique capable of reducing a ring artifact in the X-ray examination apparatus of the embodiment mode 1. In this embodiment mode of the present invention, since the following condition (A) may be satisfied, the ring artifact may be reduced in such a case that the viewing field enlargement imaging operation is not carried out. In this condition (A), while rotary imaging data for 1 time is acquired, the straight movement table is moved only by such an amplitude which is larger than at least a linear sampling interval. This linear sampling interval is determined by an element array of an X-ray detector. It should also be noted that since the above-explained condition (A) is automatically satisfied during the viewing field enlargement imaging operation, the ring artifact can be conspicuously reduced.

Another solution of the formula (10) becomes equal to the formula (19), and the absolute value "K" of the acceleration speed becomes the formula (20). The absolute value K of the acceleration speed is equal to a half value in the case of the formula (17).

Figure 7:
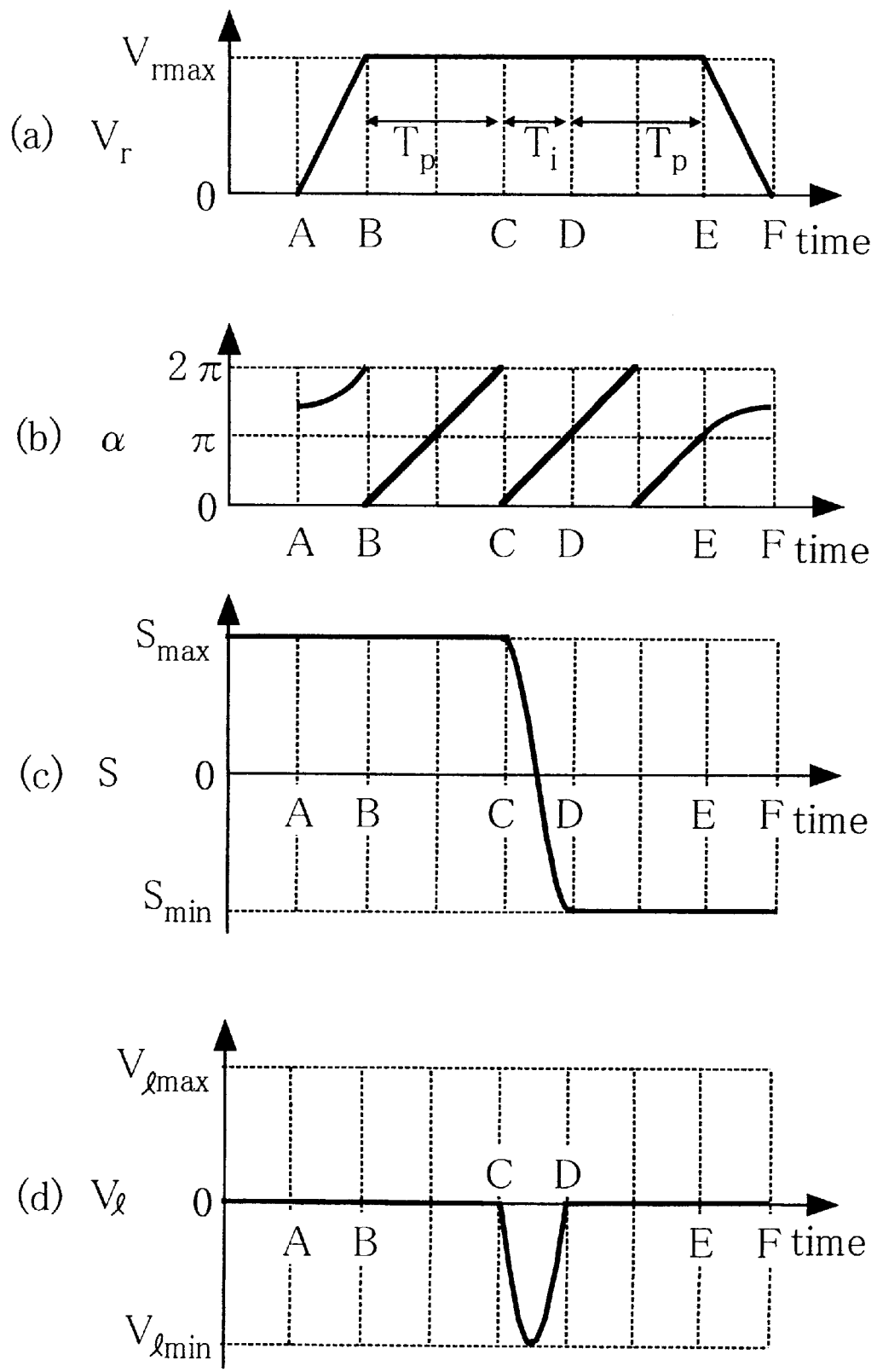
FIG. 7 is a time chart for explaining such a movement case that while the rotary imaging operation is carried out two times, a position is fixed, whereas a straight movement is carried out only in an interval between the first rotary imaging operation and the second rotary imaging operation.

FIG. 7 shows a time chart of an imaging sequence executed in accordance with the above-explained formula (19). FIG. 7(a) indicates a temporal change of the rotation speed $V_r$ (rad/sec); FIG. 7(b) represents a temporal change of the rotary angle "α" (rad); FIG. 7(c) denotes a temporal change of the position S of the straight movement table; and FIG. 7(d) indicates a temporal change of the speed $V_l$ of the straight movement table. In the sequence shown in FIG. 7, when the rotary imaging operation of the second time is carried out, the position of the straight movement table is fixed, whereas the straight movement table is moved along the straight direction only within the interval CD between the first rotation and the second rotation. A trail ⑥ of the gravity center ($S_0$) of the examination object in the control shown in FIG. 7 is represented in FIG. 6(b). As apparent from FIG. 6(b), also in the sequence shown in FIG. 7, the load given to the examination object can be reduced, and furthermore, lowering of the spatial resolution caused by the movement of the examination object can be prevented.

Numeral values employed in a concrete example of the movement condition of the examination object movement table shown in FIG. 7 and FIG. 6(b) are represented as follows:

$S_{max}$=50 (mm), $S_{min}$=−50 (mm), $T_p$=2π (sec), $T_i$=π (sec), β=1 (rad/sec), $V_{lmax}$=50 (mm/sec), $V_{lmin}$=−50 (mm/sec), $V_{rmax}$=1.3 (rad/sec), k=50 ((rad/sec)$^2$mm).

$$S=S_{max} \quad \text{(formula 19)}$$

$$k=\beta^2 \cdot S_{max} \quad \text{(formula 20)}$$

Figure 8:
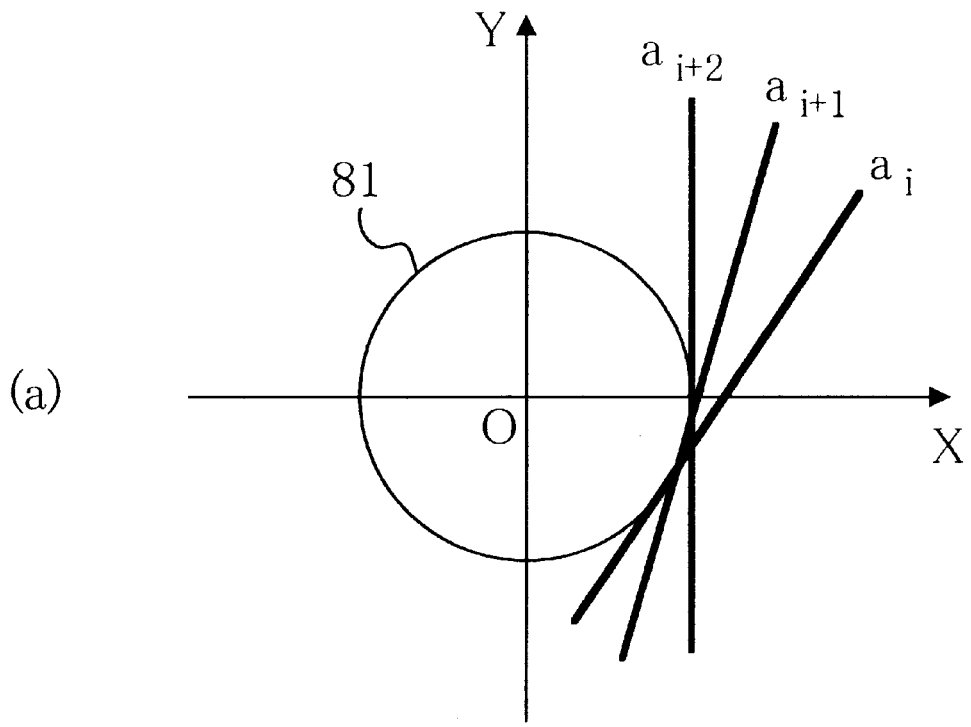
FIG. 8 is an explanatory diagram for explaining a basic idea of a method for reducing a ring artifact by moving the straight movement table in a fine mode while the rotary imaging operation is carried out.
Figure 8:
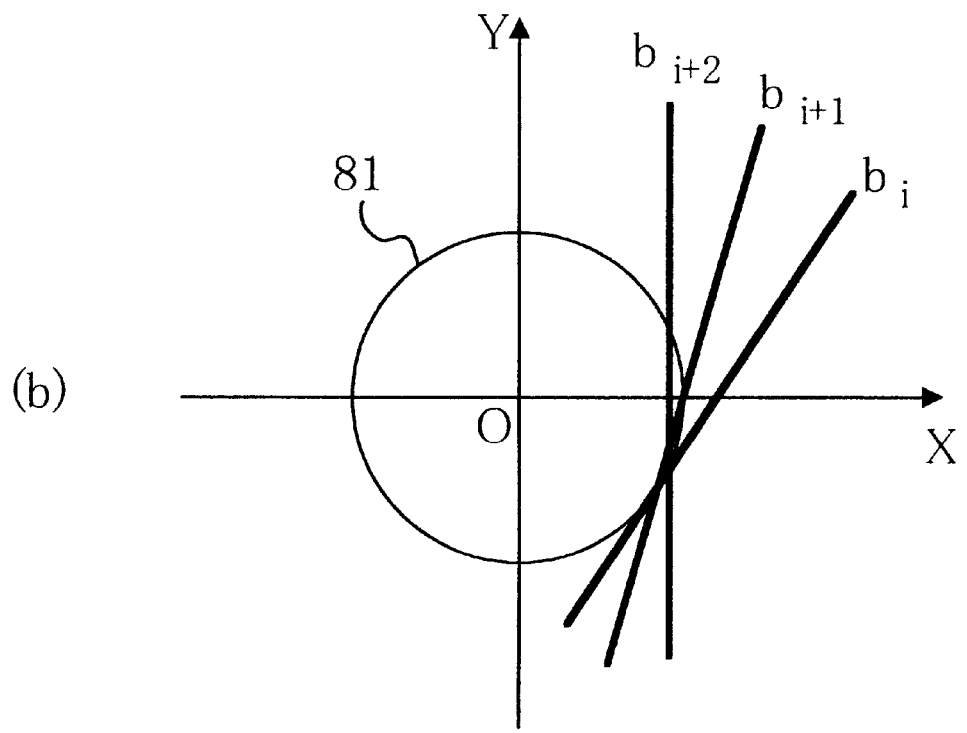

FIG. 8 is an explanatory diagram for explaining a basic idea capable of reducing a ring artifact which is caused by very fine movement of the straight movement table while the rotary imaging operation is carried out. FIG. 8(a) indicates such a case that the straight movement table is not moved during the rotary imaging operation similar to the prior art, FIG. 8(b) represents such a case that during the rotary imaging operation, the straight movement table is moved by such an amplitude. That is, this amplitude is larger than at least the linear sampling interval which is determined by the element array of the X-ray detector. It should be noted that in FIG. 8, while an origin "O" of a reconstructed image is selected to be the rotation center (center of viewing field) of the rotary table, both an abscissa and an ordinate of the reconstructed image are expressed as an X axis and a Y axis.

First, a description will now be made of such a case that the straight movement table is not moved during the rotary imaging operation similar to the prior art with reference to FIG. 8(a). In FIG. 8(a), symbols $a_i$, $a_{i+1}$, $a_{i+2}$, - - - , represent positions where images imaged in conjunction with the relative position movement of the X-ray source at an i-th order, an (i+1)-th order, an (i+2)-th order, - - - , are back-projected in a reconstruction calculation of projection data based upon an X-ray beam which connects a specific X-ray detector element of interest and the X-ray source. An envelope line 81 of these X-ray beams constitutes such a circle that the rotation center "O" is used as a center thereof. An X-ray beam group of interest is not back-projected inside of this circle. Also, an X-ray beam which is located at a position separated from the origin, as compared with the X-ray beam of the interest, is not back-projected on the envelope circle 81. As a result, an imperfect sensitivity correction with respect to the X-ray beam which is located at the position separated from the origin, as compared with the X-ray beam of the interest, may appear as the ring artifact on the envelope circle 81 on the reconstructed image. The imperfect sensitivity corrections of a plurality of detectors may cause a plurality of ring artifacts having coaxial shapes.

Next, with reference to FIG. 8(b), as indicated in the embodiment mode 1, the following case will now be described. That is, FIG. 8(b) shows such a case that during the rotary imaging operation, the straight movement table is moved by such an amplitude. That is, this amplitude is larger than at least the linear sampling interval which is determined by the element array of the X-ray detector. In FIG. 8(b), symbols $b_i$, $b_{i+1}$, $b_{i+2}$, - - - , show positions where images imaged in conjunction with the relative position movement of the x-ray source at an i-th order, an (i+1)-th order, an (i+2)-th order, . . . , are back projected in a reconstruction calculation of projection data based upon an X-ray beam which connects a specific X-ray detector element of interest and the X-ray source. Since the straight movement table is moved during the rotary imaging operation, distances of the respective X-ray beams from the origin are changed. During the reconstruction image calculation, such an envelope line does not appear which constitutes a coaxial circle where the rotation center "O" is set as a center. As a result, a ring artifact appearing on the reconstructed image is reduced. Since the ring artifact readily appears at the position in the vicinity of the rotation center in the reconstructed image, there is a great merit that the ring artifact located near the rotation center can be especially reduced as to the movement during the rotary imaging operation.

Next, a description will now be made of such a technique capable of reducing a streek artifact in the embodiment mode 1. This streek artifact is caused by that a total number of projection images is finite during a rotary imaging operation in such a case that a viewing field shape of an image reconstruction is not equal to a circle in which a rotation center is set as a center, for example, during a rotary imaging operation in such a case that a viewing field shape of an image reconstruction is an ellipse. The reduction of the streek artifact may be realized by such an effect that when an X-ray source is located in a direction along which a viewing field radius of an image reconstruction is a maximum value, an angle interval by which an imaging operation is carried out is made smaller than a value of an equal angle interval used in the normal imaging operation.

Concretely speaking, assuming now that a time period of one rotation of an X-ray rotary imaging operation is selected to be $T_p$ seconds, a total imaging sheet acquired during one rotation is selected to be $N_r$, and interval time between a first rotation and a second rotation is selected to be $T_i$ seconds, in the sequence of FIG. 4, the streek artifact can be reduced in the viewing field enlargement imaging operation by increasing, or decreasing $T_i$ by $T_p/(2N_r)$ than $T_p/2$, namely by making:

$$T_i=(T_p/2)\cdot(1+(1/N_r)),$$

or $$T_i=(T_p/2)\cdot(1-(1/N_r)).$$

Figure 9:
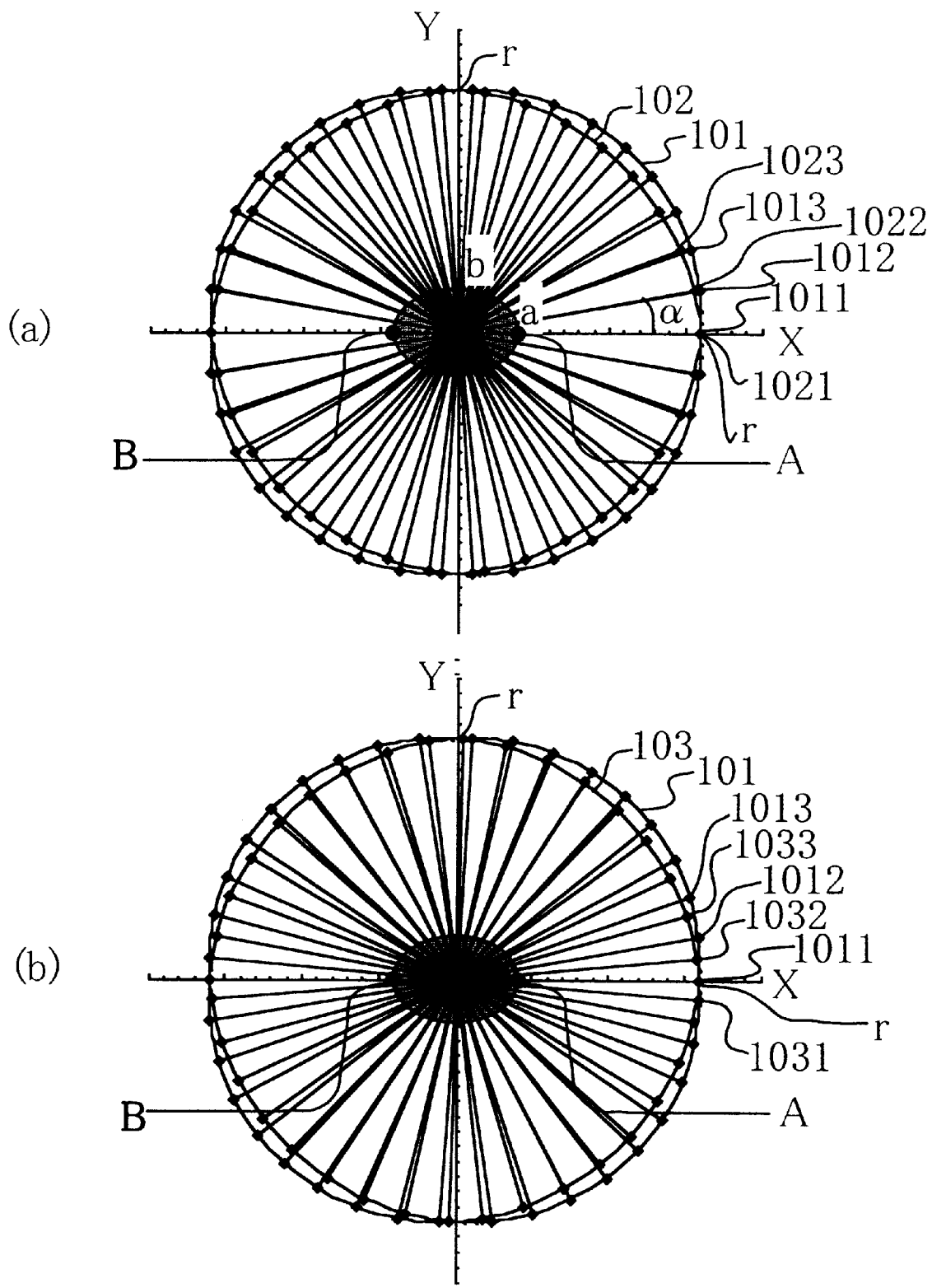
FIG. 9 is a diagram for schematically representing an improvement of an angle interval of the rotary imaging operation according to the present invention, in such a coordinate system that the center of the straight movement table is fixed.

FIG. 9 schematically shows an improvement in an angle interval of an imaging operation according to the present invention, in such a coordinate system that an examination object is fixed, namely this examination object is fixed to a center of a straight movement table. FIG. 9(a) indicates the conventional technique, namely such a case that while the rotary imaging operation is carried out two times, the rotary imaging operation is performed when the X-ray source becomes the same rotation angle (namely, rotary imaging operation is carried out every equal angle). FIG. 9(b) shows an embodiment mode of the present invention, such a case that while the rotary imaging operation is carried out two times, the following angle interval control is carried out. That is, an angle interval used to perform the rotary imaging operation when the X-ray source is located in a direction along which the viewing field radius of the image reconstruction becomes a maximum value is made smaller than an angle interval used to perform the rotary imaging operation when the X-ray source is located in a direction along which the viewing field radium of the image reconstruction becomes a minimum value.

In FIG. 9(a), a circle 101 and a circle 102 represent an orbit of the X-ray source during the rotary imaging operation of the first rotation, and an orbit of the X-ray source during the rotary imaging operation of the second rotation. Points 1011, 1012, 1013, - - - , appearing on the circle 101 show positions of the X-ray source during the rotary imaging operation of the first rotation, whereas points 1021, 1022, 1023, - - - , appearing on the circle 102 represent positions of the X-ray source during the rotary imaging operation of the second rotation. It should be noted that for the sake of a simple display, the positions of the X-ray source is displayed every 10 degrees. In the case that the X-ray source is located in the direction (X-axis direction) along which the viewing angle radius of the image reconstruction becomes the maximum value, the X-ray source position 1011 is overlapped with the X-ray source position 1021, and also the X-ray source position 1012 is located very close to the X-ray source position 1022. As a result, when the X-ray source is reached in the direction (X-axis direction) along which the viewing field radius of the image reconstruction becomes the maximum value, the angle interval of the projection becomes maximum.

In FIG. 9(b), a circle 101 and a circle 103 represent an orbit of the X-ray source during the rotary imaging operation of the first rotation, and an orbit of the X-ray source during the rotary imaging operation of the second rotation in the embodiment mode 1. Points 1011, 1012, 1013, - - - , appearing on the circle 101 show positions of the X-ray source during the rotary imaging operation of the first rotation, whereas points 1031, 1032, 1033, - - - -, appearing on the circle 103 represent positions of the X-ray source during the rotary imaging operation of the second rotation in this embodiment mode 1. It should be noted that in FIG. 9(b), the position of the X-ray source during the rotary imaging operation of the first rotation is identical to that of FIG. 9(a), and also, the position of the X-ray source during the rotary imaging operation of the second rotation is present at such a position shifted by a half of an angle through which the adjoining X-ray sources are viewed from the case of FIG. 9(a). As a result, in such a case that the X-ray source is located in the direction (X-axis direction) along which the viewing angle radius of the image reconstruction becomes the maximum value, the X-ray source position 1011 is not overlapped with the X-ray source position 1031, and also the angle interval during the rotary imaging operation at the X-ray source position 1011 and the X-ray source position 1031 is equal to a half of the angle interval during the rotary imaging operation at the X-ray source position 1011 and the X-ray source position 1012 of FIG. 9(a). As a result, when the X-ray source is reached in the direction (X-axis direction) along which the viewing field radius of the image reconstruction becomes the maximum value, the angle interval of the imaging operation becomes a half of the angle interval in the prior art of FIG. 9(a).

A position where the angle interval of the rotary imaging operation becomes the coarsest angle interval is equal to such a position where an angle through which the adjoining X-ray source positions are viewed in the rotation of the X-ray source becomes maximum. In the normal rotary imaging operation in which the viewing field is not enlarged, assuming now that the rotation radius of the X-ray source is selected to be r=40 (cm) and also the radius of the reconstruction viewing field is set to a=b=13 (cm), a maximum value of the angle interval of the imaging operation may be expressed by the following formula (21). In this formula, symbol "N" indicates a total imaging number per 1 rotation.

$$\alpha_{max} = 2\pi \cdot r / \{(r-b) \cdot N\} = 0.037037 \times 2\pi \cdot r / N \quad \text{(formula 21)}$$

When a longer radius of the reconstruction viewing field becomes "a" and a shorter radius thereof becomes "b" after the rotary imaging operation is carried out two times in the viewing field enlargement mode, such positions where the angle interval of the imaging operation shown in FIG. 9(a) becomes the coarsest interval are both a point A and a point B on the X-axis. At the position of the point A and the position of the point B, assuming now that a=18 (cm), a maximum value of the angle interval of the rotary imaging operation in the case of FIG. 9(a) becomes the following formula (22), namely becomes longer than the maximum value of the formula (21). However, in FIG. 9(b), as indicated in the formula (23), the maximum value of the angle interval is reduced to be a half maximum value of the formula (22), and becomes smaller than the value of the formula (21):

$$\alpha_{max} = 2\pi \cdot r / \{(r-a) \cdot N\} = 0.045455 \times 2\pi \cdot r / N \quad \text{(formula 22)}$$

$$\alpha_{max} = \pi \cdot r / \{(r-a) \cdot N\} = 0.022727 \times 2\pi \cdot r / N \quad \text{(formula 23)}$$

In accordance with the embodiment mode 1, in the case that the X-ray source passes through such a position where a parallel movement direction of a parallel motion mechanism is located in parallel to a direction for connecting the X-ray source and a rotation axis of a rotary movement mechanism, such a control operation is carried out as follows: That is, the direction of the X-ray entered into the examination object during the rotary imaging operation of the first rotation is shifted only by $(1/(2N_r))$ rotations from that during the rotary imaging operation of the second rotation. In other words, since such a control operation is performed in such a manner that the parallel movement direction of the parallel motion mechanism is shifted by $(\pi/N_r)$ radians, it is possible to avoid the overlapping operations of the imaging operations along the angle direction, and also the artifact caused by the projection total number can be reduced. Furthermore, in the embodiment mode 1, since the above-explained condition (A) can be satisfied by adjusting the timing between the camera and the X-ray control system, the artifact can be easily reduced.

Figure 10:
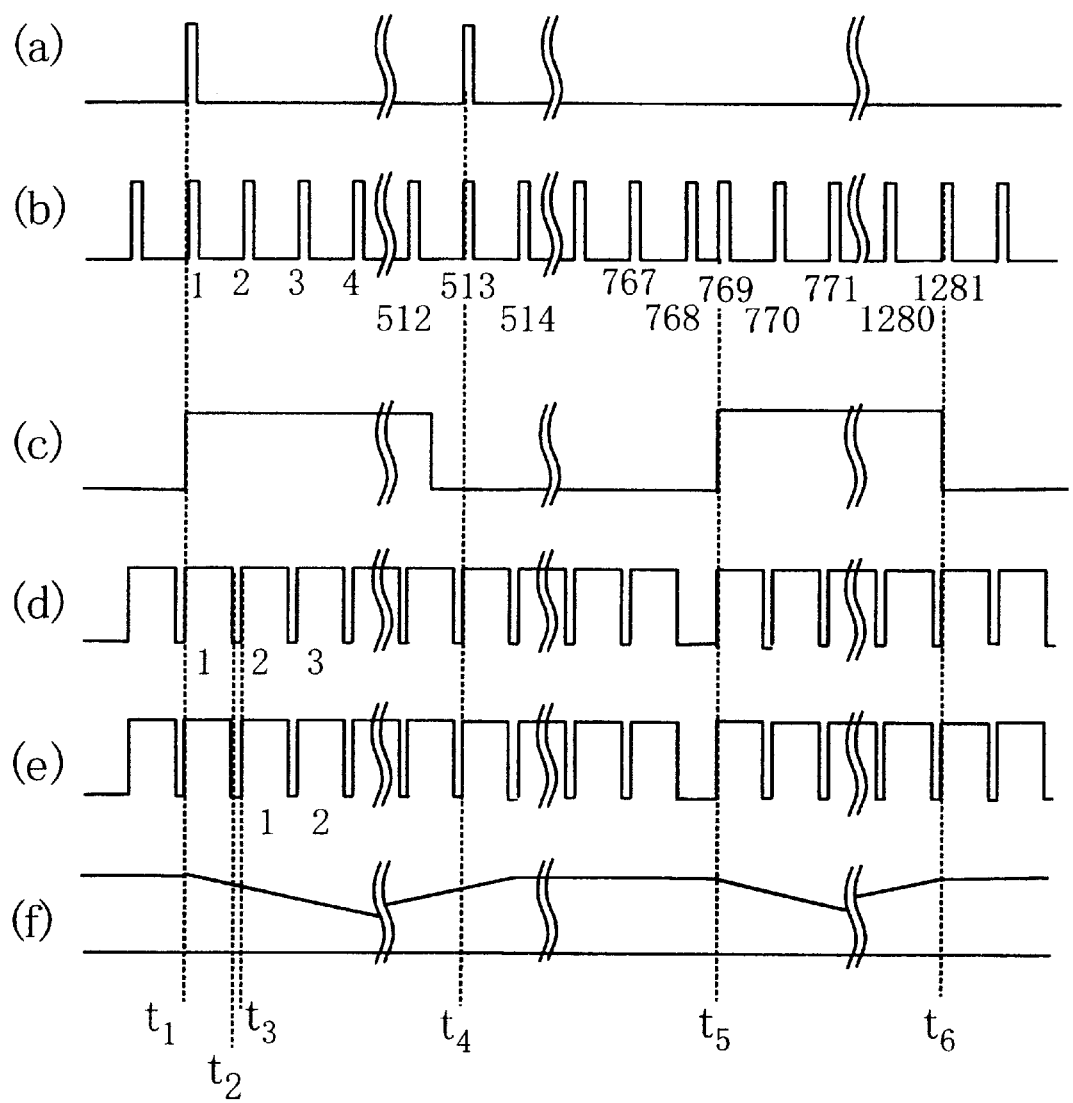
FIG. 10 is an example of a time chart for an imaging sequence according to the embodiment mode 1.

FIG. 10 is an example of a time chart for showing an imaging sequence of the embodiment mode 1. Referring now to FIG. 10, operations of the X-ray examination apparatus according to the embodiment mode 1 will be described. FIG. 10(a) represents a reference rotation angle signal (rotation angle zero signal); FIG. 10(b) shows an external synchronization signal produced by the rotary imaging control apparatus; FIG. 10(c) denotes an X-ray irradiation condition; FIG. 10(d) represents operation for storing electron charges into a CCD (simply referred to as a "CCD storage" hereinafter); FIG. 10(e) shows operation for reading a signal from the CCD (simply referred to as a "CCD readout" hereinafter); and FIG. 10(f) indicates a coordinate system of the straight movement table. Also, an abscissa shows time.

When the reference rotation angle signal which constitutes a reference angle signal is detected by the synchronization signal generating unit 512, the external synchronization signal is produced ($t_1$). This time instant "$t_1$" corresponds to the time instant "B" of FIG. 4. In synchronism with the produced external synchronization signal, the X-ray irradiation, the CCD storage of the first image, and the movement of the straight movement table are commenced. The operation time of the CCD storage is set to, for example, 16 msec. When this CCD storage is ended ($t_2$), the CCD readout of the first image is subsequently commenced ($t_3$), and the image is read out for 16.7 msec, and then the read image is stored into the frame memory.

Subsequently, in response to an angle signal (every 8 pulses of encoder output from 12-bit incremental angle encoder) every degree (360°/150=0.703125°) (omitted in the description), the synchronization signal generating unit 512 generates external synchronization signals after the second external synchronization signal. In synchronism with a 513-th external synchronism signal (corresponding to time instant C of FIG. 4), both the movement of the straight movement table and the X-ray projection are stopped ($t_4$). At this time instant $t_4$, the rotation of the rotation table 22 is continued.

Next, the synchronization signal generating unit 512 generates only a 769-th external synchronization signal (corresponding to time instant D of FIG. 4) in synchronism with an angle signal having a half of angle difference (360°/1024=0.3515625) (4 pulses of above-explained angle encoder) (time instant $t_5$). As a result, the timing of the imaging operation of the second rotation is shifted only by an angle equal to a half of an angle interval of the imaging operation with respect to the timing of the imaging operation of the first rotation, so that the angle interval of the imaging operation can be reduced. In response to the 769-th external synchronization signal, the X-ray irradiation of the second rotation, the CCD storage, and the movement of the straight movement table are started. In synchronization to a 1281-th external synchronization signal (corresponding to time instant E of FIG. 4), the movement of the straight movement table and the X-ray projection are stopped, and then, a series of the rotary imaging operations are accomplished ($t_6$).

It should be noted that the aperture of the iris 361 is set in accordance with the following manner. In a series of the rotary imaging operation, the aperture of the iris 361 (simply referred to as an "iris target value" hereinafter) set in the imaging operation of the (n+2)-th image is predicted in parallel to the signal reading operation from the CCD of the n-th image. The iris target value prediction is carried out in such a manner that the maximum pixel value of the (n+2)-th image is made coincident with a preset value based upon a relationship among the maximum pixel values at the regions of interest set to both the (n−1)-th images and the n-th image, the apertures of the iris 361 set during the imaging operations of the (n−1)-th image and the n-th image, the aperture of the iris 361 set as the initial value, and the iris area and the iris aperture, which are previously set. The time duration required for changing the area of the iris must be set shorter than such a time duration defined by subtracting a time duration required to calculate the iris target value from the CCD readout time. As a consequence, in the embodiment mode 1, the CCD readout time is equal to 16.7 msec per 1 frame, whereas the calculation time required to predict the iris target value is nearly equal to 0.2 msec, and the time duration required for changing the area of the iris is limited to 10 msec in maximum.

(Embodiment Mode 2)

Figure 11:
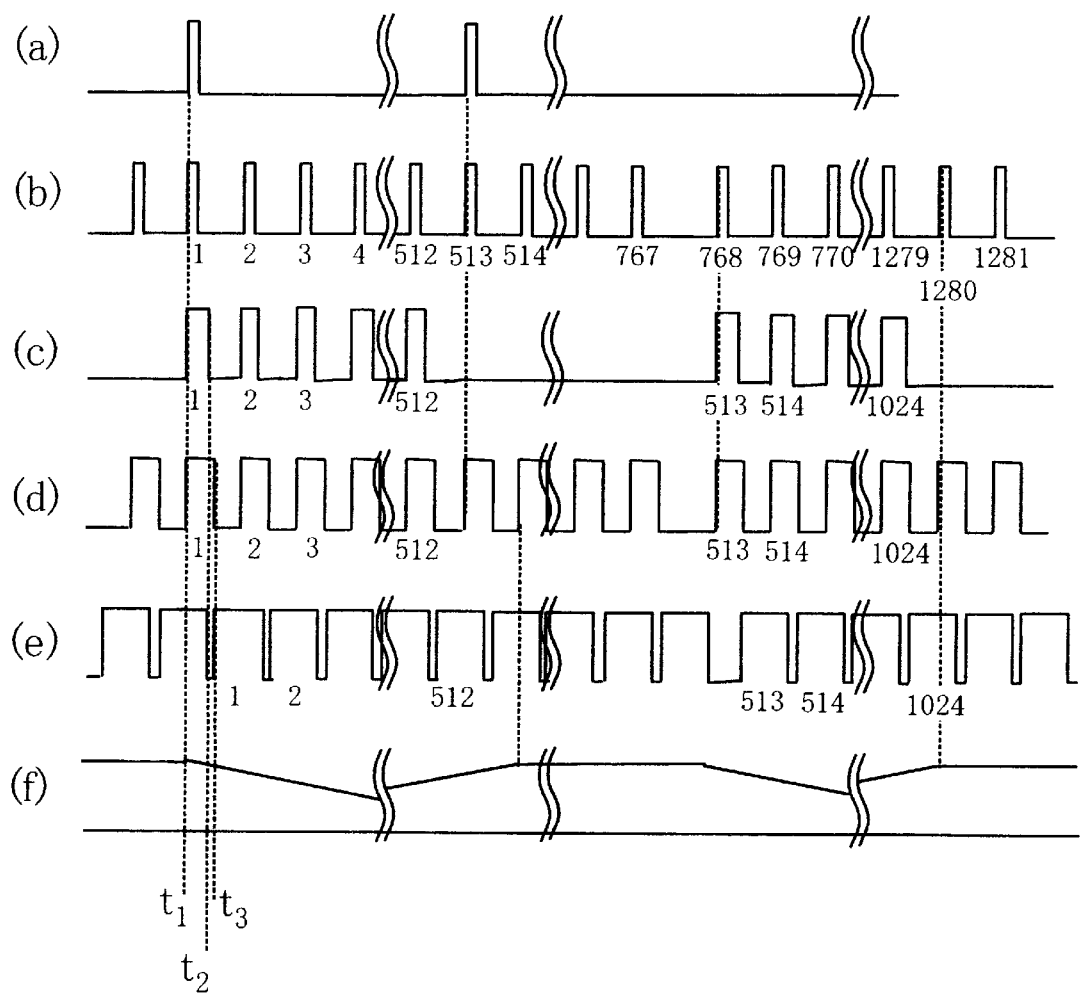
FIG. 11 is a time chart of an imaging sequence according to the embodiment mode 2 of the present invention.

FIG. 11 is a time chart for showing an imaging sequence according to an embodiment mode 2 of the present invention. Similar to FIG. 10, FIG. 11(a) represents a reference rotation angle signal (rotation angle zero signal); FIG. 11(b) shows an external synchronization signal produced by the rotary imaging control apparatus; FIG. 11(c) denotes an X-ray irradiation condition; FIG. 11(d) represents operation for storing electron charges into a CCD; FIG. 11(e) shows operation for reading a signal from the CCD; and FIG. 11(f) indicates a coordinate system of the straight movement table. Since an arrangement of an X-ray examination apparatus according to the embodiment mode 2 is identical to that of the X-ray examination apparatus according to the embodiment mode 1, an explanation thereof is omitted.

The X-ray examination apparatus of the embodiment mode 2 is featured by that a pulse X-ray is irradiated to an examination object. In other words, when the reference rotation angle signal which constitutes a reference angle signal is detected by the synchronization signal generating unit 512, the external synchronization signal is produced ($t_1$). In synchronism with the produced external synchronization signal, the X-ray irradiation, the CCD storage of the image, and the movement of the straight movement table are commenced. Next, the irradiation of the pulse X-ray is ended ($t_2$), and thereafter the CCD storage is ended ($t_3$). Subsequently, in response to the external synchronization signal, the irradiation of the pulse X-ray and the CCD storage of the image, the irradiation of the pulse X-ray and the CCD storage are repeatedly accomplished, so that the X-ray images along the plural directions are sequentially imaged, and then, the X-ray images are stored into the frame memory. It should be noted that since other sequence portions are similar to the imaging sequence according to the embodiment mode 1 shown in FIG. 10, explanations thereof are omitted. In this embodiment mode 2, as the operation time of the CCD storage, for example, this operation time is set to, for example, 6 msec which is longer than 5.5 msec corresponding to the maximum width value of the pulse X-ray.

It should also be noted that in a series of rotary imaging operations, only the aperture of the iris 361 is controlled in the embodiment mode 1, whereas both the width of the pulse X-ray and the aperture of the iris can be controlled. Alternatively, only one of both the width of the pulse X-ray and the aperture of the iris may be controlled.

Both a maximum pixel value of an (n+2)-th image and a minimum pixel value thereof are predicted based upon a relationship among an initially set width of a pulse X-ray; an initially set aperture of an iris; the aperture of the iris 361 and the width of the pulse X-ray, which are set during the imaging operations of the previously imaged (n−1)-th image and (n)-th image; both a maximum pixel value and a minimum pixel value in the regions of interests set to both the (n−1)-th image and the (n)-th image; both a maximum pixel value and a minimum pixel value in a region of interest which is set to such an image imaged under condition with respect to both the initially set width of the pulse X-ray and the initially set aperture of the iris; and furthermore, both a preset iris area and a preset aperture. Then, both the aperture of the iris 361 and the width of the pulse X-ray are controlled to be changed in such a manner that the maximum pixel value of the (n+2)-th image is made coincident with the preset maximum value.

In accordance with the X-ray examination apparatus of the embodiment mode 2, the same effect as that of the embodiment mode 1 can be achieved. Furthermore, since the pulse X-ray is irradiated to the examination object only during the imaging time in the X-ray examination apparatus of the embodiment mode 2, there is another effect that the X-ray projection amount of the examination object can be reduced in addition to the effect of the X-ray examination apparatus according to the embodiment mode 1.

(Embodiment Mode 3)

Figure 12:
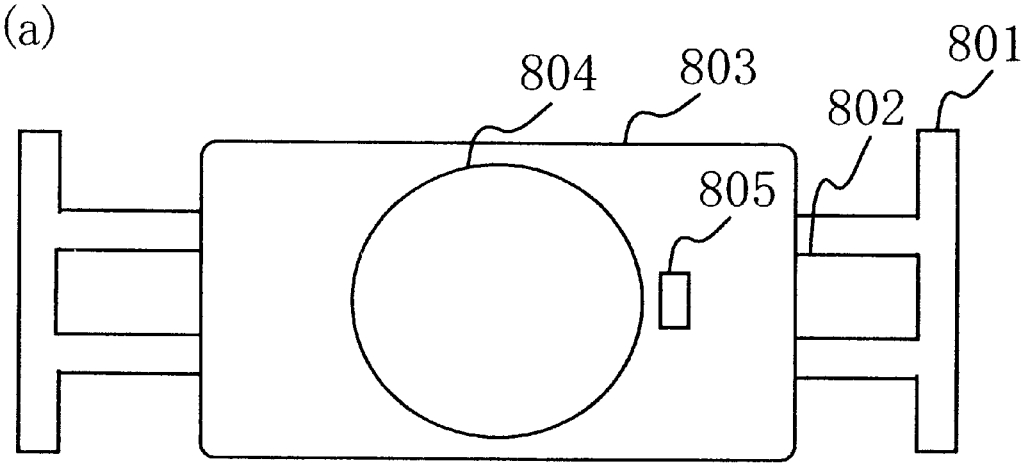
FIG. 12 is an explanatory diagram for explaining a schematic arrangement of an examination object supporting system portion of a cone-beam CT apparatus corresponding to an embodiment mode 3 of the present invention.
Figure 12:
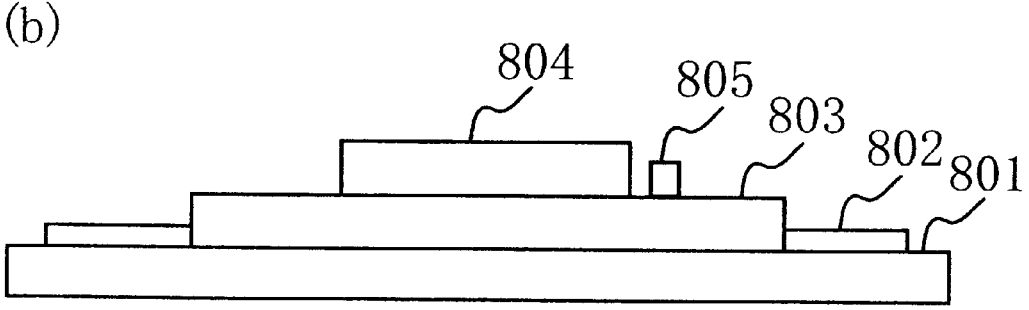

FIG. 12 is an explanatory diagram for explaining a schematic arrangement of a portion of an examination object supporting system for a cone-beam CT apparatus corresponding to an X-ray examination apparatus according to an embodiment mode 3 of the present invention. FIG. 12(a) is an upper view, and FIG. 12(b) is a side view. It should be understood that in accordance with the X-ray examination apparatus of the embodiment mode 3, only an imaging sequence and an acquisition order of X-ray images are different from those of the embodiment mode 1, which are caused by a different arrangement of an examination object supporting system 2 and also this arrangement of the examination object supporting system 2 is different from that of the embodiment mode 1. Other arrangements of this X-ray examination apparatus according to the embodiment mode 3 are identical to those of the embodiment mode 1. Accordingly, only different portions will now be explained. It should also be noted that as to an algorithm used to reconstruct both a tomographic image and also a three-dimensional image from X-ray images which are imaged by the X-ray examination apparatus of the embodiment mode 3, only an acquisition order of the X-ray images is different from that of the embodiment mode 1, and other algorithm portions are identical to those of the embodiment mode 1. Therefore, descriptions of this algorithm are omitted.

In FIG. 12, reference numeral 801 shows a supporting member of a straight movement table; reference numeral 802 indicates a rail of the straight movement table; reference numeral 803 represents the straight movement table; reference numeral 804 denotes a rotary table; and reference numeral 805 shows a reference rotation angle detecting means. In the arrangement of the examination object supporting system 2 of the embodiment mode 3, the rotary table 804 is set on the straight movement table. Concretely speaking, two sets of rails 802 are arranged in a parallel manner on the side of the upper surface of the straight movement supporting member 801, and also the straight movement table 803 is mounted on the rail 802. Both the rotary table 804 and the reference rotation angle detecting means 805 are arranged on the side of the upper surface of the straight movement table 803. It should also be noted that the basic arrangements of the straight movement table 803 and of the rotary table 804 are identical to those of both the straight movement table 23 and the rotary table 22 of the embodiment mode 1, and these straight movement table 803 and the rotary table 804 are operated in response to the control signal entered via the rotary/straight movement table interface 517.

In comparison with such a structure that the straight movement table 23 is mounted on the rotary table 22 shown in the embodiment mode 1, since the mechanical load given to the rotary table 804 is small in the examination object supporting system according to the embodiment mode 3, there is such a merit that the rotary table 804 can be made compact as well as in low cost, and is practically utilized.

FIG. 6(c) shows a trail ⑦ of a center of the rotary table mounted on the straight movement table. In the embodiment mode 3, the center of the rotary table is moved in the reciprocation manner on the straight line (X axis) in accordance with the formula (16). It should also be noted that the movement sequence of the embodiment mode 3 is completely identical to that of the embodiment mode 1 shown in FIG. 4. In this embodiment mode 3, an acceleration speed of a center of an examination object becomes only a component along the X-axis direction, and is expressed by the following formula (24). In other words, a magnitude of this acceleration speed is changed in connection with the time elapse. However, a maximum value of absolute values of the acceleration speeds becomes the formula (20), namely is equal to a half of the formula (17). As a consequence, the practical control operation can be carried out in this embodiment mode 3, namely it is possible to reduce the load with respect to the examination object.

$$a_x = S_{max} \cdot \beta^2 \cdot \cos(\beta \cdot t) \quad \text{(formula 24)}$$

The numeral values employed in a concrete example as to the movement condition of the examination object movement table indicated in FIG. 8 and FIG. 6(c) are described as follows: $S_{max}$=50 (mm), $S_{min}$=−50 (mm), $T_p$=2π (sec), $T_i$=π (sec), β=1 (rad/sec), $V_{lmax}$=50 (mm/sec), $V_{lmin}$=−50 (mm/sec), k=50 ((rad/sec)$^2$mm).

As previously explained, in the X-ray examination apparatus according to the embodiment mode 3, the mechanical load given to the rotary table 804 is small because of the arrangement of the examination object supporting system 2 for mounting the rotary table 80 on the straight movement table. Thus, the rotary table 804 can be made compact and in low cost. As a consequence, the X-ray examination apparatus can be made compact as well as in low cost.

An X-ray imaging method of an X-ray image, according to the present invention, is featured by comprising: a step in which while an examination object is rotated on a straight line for connecting a focal point of an X-ray tube to a center of an X-ray detector positioned opposite to the X-ray tube, the examination object is moved in a direction parallel to a rotation plane in synchronism with a rotation period, and an X-ray image of the examination object is imaged along a plurality of directions during the rotating operation and the moving operation of the examination object; a step for producing an X-ray tomographic image and/or an X-ray 3-dimensional image; and a step for displaying the X-ray tomographic image and/or the X-ray 3-dimensional image.

Also, an X-ray imaging method of an X-ray image, according to the present invention, is featured by comprising: a step in which while an examination object is rotated on a straight line for connecting a focal point of an X-ray tube to a center of an X-ray detector positioned opposite to the X-ray tube, the examination object is moved in a direction perpendicular to a rotation plane and also in a direction parallel to the rotation plane in synchronism with a rotation period, and an X-ray image of the examination object is imaged during the rotating operation and said moving operation of the examination object; a step for producing an X-ray tomographic image and/or an X-ray 3-dimensional image from the X-ray images of the examination object imaged along a plurality of directions; and a step for displaying the X-ray tomographic image and/or the X-ray 3-dimensional image.

It should be noted that although the embodiment modes employ the detector constructed of the X-ray I.I. and the television camera, other arrangements may be employed. For example, a 2-dimensional detector constructed of a TFT, or a 1-dimensional detector may be apparently employed.

Also, apparently, the present invention may be applied to a medical X-ray examination apparatus for imaging general living things such as a human body, and also to an X-ray baggage examination apparatus for imaging X-ray images of air line baggages. While the present invention is applied to an X-ray baggage examination apparatus, a baggage can be imaged while an acceleration speed applied to this baggage is kept constant during the imaging operation. As a consequence, since movement of contents contained in such a baggage can be suppressed as being permitted as possible, this X-ray baggage examination apparatus can prevent an occurrence of an artifact caused by such movement of the contents.

While the present invention has been described with reference to the various concrete embodiment modes, the present invention is not limited to these embodiment modes, but may be modified, changed, or substituted without departing from the technical scope and spirit of the present invention.

The typical effects achieved by the disclosed present invention will now be briefly explained as follows:

(1) the viewing field of the X-ray fluoroscopic image, the x-ray imaging image, or the X-ray tomographic image, acquired under standing position, or sitting position can be enlarged.

(2) the viewing field of the stereoscopic image (3-dimensional image) acquired under standing position, or sitting position can be enlarged.

(3) the installation area of the examination object rotation type X-ray examination apparatus can be reduced.

(4) the stereoscopic image having the high image quality acquired under standing position, or sitting position can be obtained.
(5) the load given to the examination object can be reduced.
(6) the time required for performing the imaging operation can be shortened.
(7) the ring artifact can be reduced.
(8) the streek artifact caused by limiting a total projection number can be reduced.

What is claimed is:

1. An X-ray examination apparatus comprising:
   X-ray generating means for generating an X-ray which irradiates an examination object;
   imaging means positioned opposite to an X-ray tube of said generating means, for detecting an X-ray image of said examination object;
   supporting means for supporting said examination object;
   moving means
      for causing straight movement of said supporting means, wherein said moving means is comprised of reciprocation moving means for causing reciprocation straight movement of said supporting means and period controlling means for controlling a period of said reciprocation straight movement; and
   rotating means for rotating said movement at a preselected speed, said moving means being installed above said rotating means;
   wherein said reciprocating moving means causes said reciprocation straight movement of said supporting means in parallel to a rotation plane of said rotating means, said period controlling means controls to make a period of said reciprocation straight movement coincident with a rotation period of said rotation means; and
   wherein, while said examination object is rotated, the position of said examination object is moved along a direction parallel to said rotation plane, and the X-ray image of the examination object are detected during the rotation of said rotating means and the movement of moving means, and an X-ray tomographic image and/or an X-ray three-dimensional image of said examination object are produced from the X-ray images detected at a plurality of rotation angles of said rotating means, and then said X-ray tomographic image and/or said X-ray three-dimensional image are displayed.

2. An X-ray examination apparatus as claimed in claim 1, further comprising:
   control means for performing a control in such a manner that, while said supporting means is rotated for one rotation having as a starting point where a rotation speed of said rotating means becomes constant, and said examination object is moved from a maximum moving position of the reciprocation straight movement by said reciprocating moving means, the X-ray images are detected during the rotation of said rotating means and said reciprocation straight movement by said reciprocating moving means; and
   while said supporting means is rotated for one rotation having a second starting point where said rotating means is rotated by a ½ rotation from the first starting point, and said examination object is moved from the maximum moving position of the reciprocation straight movement by said reciprocating moving means, said X-ray images are detected during said rotation of said rotating means and said reciprocation straight movement.

3. An X-ray examination apparatus as claimed in claim 2, wherein said control means controls the moving position of said examination object in accordance with such a cosine function that has an amplitude defined by a distance from a first maximum moving position by said reciprocation moving means at one side to a second maximum moving position by said reciprocating moving means at the other side, said first maximum moving position at one side or said second maximum position at the other side is used as the first starting point.

4. An X-ray examination apparatus comprising:
   X-ray generating means for generating an X-ray which irradiates an examination object;
   imaging means positioned opposite to an X-ray tube of said generating means, for detecting an X-ray image of said examination object;
   supporting means for supporting said examination object;
   moving means for causing straight movement of said supporting means;
   rotating means for rotating said moving means at a preselected speed, said moving means being installed above said rotating means; and
   control means for performing a control said moving means and said rotating means in such a manner that directions of the X-ray entered into the examination object are not coincident during a first rotation of said rotating means and a second rotation of said rotating means;
   wherein, while said examination object is rotated, the position of said examination object is moved along a direction parallel to a rotation plane of said rotating means, and the X-ray images of the examination object are detected during the rotation of said rotating means and the movement of said moving means, and an X-ray tomographic image and/or an X-ray three-dimensional image of said examination object are produced from the X-ray images detected at a plurality of rotation angles of said rotating means, and then said X-ray tomographic image and/or said X-ray three-dimensional image are displayed.

5. An X-ray examination apparatus as claimed in claim 4, further comprising:
   control means for performing a control in such a manner that an interval of detecting the X-ray images between the detection of the X-ray image at the first rotation and the detection of the X-ray image at the second rotation with respect to the rotation angle of said rotating means is different by a ½ angle between an imaging angle and a next imaging angle at a preselected rotation angle.

6. An X-ray examination apparatus as claimed in claim 4, further comprising:
   control means for performing a control in such a manner that assuming now that time required for rotating said supporting means for one rotation by said rotating means is selected to be $T_p$ seconds, a total number of the X-ray images detected while said examination object is rotated for one rotation is selected to be $N_r$, and an interval of detection of said X-ray images is selected to be $T_i$ seconds, said interval $T_i$ becomes equal to:

$$T_i=(T_p/2)\cdot(1+(1/N_r)),$$

or $$T_i=(T_p/2)\cdot(1-(1/N_r)).$$

7. An X-ray imaging method of an X-ray image comprising the steps of:
   a step in which, while an examination object is rotated on a rotary table on a straight line connecting a focus of an X-ray tube and a center of a two-dimensional X-ray image detector positioned opposite to said X-ray tube, said examination object is moved on said straight line in a direction parallel to a rotation plane of said rotating table synchronized with a rotation period of said rotating table, and X-ray images of said examination object are detected at a plurality of rotation angles during the rotation of said rotating table and at a plurality of positions of the movement of said examination object on said straight line;
   a step for producing an X-ray tomographic image and/or an X-ray three-dimensional image of said examination object; and
   a step for displaying said X-ray tomographic image and/or said X-ray three-dimensional image.

8. An X-ray imaging method of an X-ray image comprising the steps of:
   a step in which, while an examination object is rotated on a rotary table on a straight line connecting a focus of an X-ray tube and a center of a two-dimensional X-ray image detector positioned opposite to said X-ray tube, said examination object is moved on said straight line in a direction perpendicular to a rotation plane of said rotating table and in a direction parallel to said rotation plane synchronized with a rotation period of said rotating table, and X-ray images of said examination object are detected at a plurality of rotation angles during the rotation of said rotating table and at a plurality of positions of the movement of said examination object on said straight line and in the direction perpendicular to said rotation plane;
   a step for producing an X-ray tomographic image and/or an X-ray three-dimensional image of said examination object; and
   a step for displaying said X-ray topographic image and/or said X-ray three-dimensional image.

9. An X-ray examination apparatus comprising:
   an X-ray tube for producing an X-ray which irradiates an examination object;
   a X-ray tube support member for fixing said X-ray tube on a preselected position in a space above a floor plane;
   a two-dimensional X-ray image detector positioned opposite to said X-ray tube, for detecting an X-ray image of said examination object;
   a detector support member for holding said two-dimensional X-ray image detector at a preselected position in the space above the floor plane;
   a supporting member for supporting said examination object;
   a straight movement table for causing straight movement of said supporting member;
   a rotary table for supporting said straight movement table and for rotating said straight movement table at a preselected speed, said straight movement table being installed above said rotary table; and,
   a controller which controls to make a period of a reciprocation straight movement of said straight movement table coincident with a rotation period of said rotary table,
   wherein, while said examination object is rotated, the position of said examination object is moved along a direction parallel to a rotation plane of said rotary table synchronized with a rotation period of rotary table, and said X-ray images are detected, and an X-ray tomographic image and/or an three-dimensional image of said examination object are produced from the X-ray images detected at a plurality of rotation angles of said rotary table, and then said X-ray tomographic image and/or said three-dimensional image are displayed.

10. An X-ray examination apparatus according to claim 9, wherein said controller performs a control in such a manner that, while said rotary table is rotated for one rotation having as a first starting point where a rotation speed of said rotary table becomes constant, and said examination object is moved from a maximum moving position of the reciprocation straight movement by said straight movement table, the X-ray images are detected during the rotation of said rotating rotary table and said reciprocation straight movement by said straight movement table; and, while said rotary table is rotated for one rotation having a second starting point where said rotary table is rotated by ½ rotation from the first starting point, and said examination object is moved from the maximum moving position of the reciprocation straight movement by said straight movement table, said X-ray images are detected during said rotation of said rotary table and said reciprocation straight movement.

11. An X-ray examination apparatus as claimed in claim 10, wherein said controller controls the moving position of said examination object in accordance with such a cosine function that has an amplitude defined by a distance from a first maximum moving position by said straight movement table at one side to a second maximum moving position by said straight movement table at the other side, said first maximum moving position at one side or said second maximum position at the other side is used as the first starting point.

12. An X-ray examination apparatus according to claim 9, wherein said controller performs a control in such a manner that a gravity of said examination object is moved on two circular trail each having a different center.

13. An X-ray examination apparatus according to claim 9, wherein said controller performs a control a first rotation and a second rotation of said rotary table in such a manner that, while said rotary table is rotated in the first rotation for one rotation having as a first starting point where a rotation speed of said rotary table becomes constant, the X-ray images are detected during the rotation of said rotary table in a state where said straight movement table is fixed; while said rotary table is rotated in the second rotation for one rotation having a second starting point where said rotary table is rotated by ½ rotation from the first starting point, said X-ray images are detected during the rotation of said rotary table in the state where said straight movement table is fixed; and said examination object is moved from a first maximum moving position by said straight movement table at one side to a second maximum moving position by said straight movement table at the other side.

14. An X-ray examination apparatus according to claim 9, wherein said controller performs a control in such a manner that a gravity of said examination object is moved on half of a circular.

15. An X-ray imaging method of an X-ray image comprising the steps of:
   detecting X-ray images of an examination object on a supporting member supporting said examination object, while said examination object on said supporting member is rotated at a preselected speed on a rotary table above which a straight movement table causing straight movement of said supporting member is installed and the position of said examination object is moved by a straight movement of said straight movement table along a direction parallel to a rotation plane of said rotary table synchronized with a rotation period of said rotary table;

producing an X-ray tomographic image and/or an X-ray three-dimensional image of said examination object from the X-ray images; and displaying said X-ray tomographic image and/or said X-ray three-dimensional image, wherein the X-ray images of said examination object are detected at a plurality of rotation angles during the rotation of said rotating table and at a plurality of positions of the movement of said examination object along the direction parallel to the rotation plane.

16. An X-ray imaging method of an X-ray image according to claim 15, further comprising the step of:

controlling a movement of said rotating table and said straight movement table in such a manner that a gravity of said examination object is moved on two circular trail each having a different center.

17. An X-ray imaging method of an X-ray image according to claim 15, further comprising the step of:

controlling a movement of said rotating table and said straight movement table in such a manner that a gravity of said examination object is moved on half of a circular.

18. An X-ray imaging method of an X-ray image comprising the steps of:

detecting X-ray images of an examination object on supporting member supporting said examination object, while said examination object on said supporting member installed above a rotary table is rotated at a preselected speed and a position of said examination object is moved by a straight movement of a straight movement table on a straight line connecting a focal point of said X-ray tube and a center of a two-dimensional X-ray image detector, synchronized with a rotation period of said rotary table;

producing an X-ray tomographic image and/or an X-ray three-dimensional image of said examination object from the X-ray images; and displaying said X-ray tomographic image and/or said X-ray three-dimensional image, wherein the X-ray images of said examination object are detected at a plurality of rotation angles during the rotation of said rotating table and at a plurality of positions of the movement of said examination object along the direction parallel to the rotation plane.

19. An X-ray examination method according to claim 18, further comprising the step of:

controlling a movement of said rotating table and said straight movement table in such a manner that a center of said rotary table is moved in a reciprocation manner on said straight line.

* * * * *